United States Patent [19]

Sato et al.

[11] Patent Number: 5,403,948
[45] Date of Patent: Apr. 4, 1995

[54] 5-SUBSTITUTED-2,4-DIPHENYLPYRIMIDINE DERIVATIVES, THEIR PRODUCTION AND USE

[75] Inventors: Junichi Sato, Osaka; Yuzuru Sanemitsu, Hyogo; Shinichi Kawamura, Osaka, all of Japan

[73] Assignee: Sumitomo Chemical Company, Limited, Osaka, Japan

[21] Appl. No.: 279,189

[22] Filed: Jul. 22, 1994

Related U.S. Application Data

[60] Division of Ser. No. 106,604, Aug. 16, 1993, Pat. No. 5,349,108, which is a division of Ser. No. 972,806, Nov. 6, 1992, Pat. No. 5,270,467, which is a division of Ser. No. 809,649, Dec. 17, 1991, Pat. No. 5,190,575, which is a continuation of Ser. No. 602,833, Oct. 23, 1990, which is a continuation-in-part of Ser. No. 544,089, Jun. 22, 1990, abandoned, which is a continuation of Ser. No. 391,016, Aug. 9, 1989, abandoned, said Ser. No. 602,833, is a continuation-in-part of Ser. No. 508,446, Apr. 13, 1990, abandoned, which is a division of Ser. No. 391,016, Aug. 9, 1989, abandoned.

[30] Foreign Application Priority Data

Oct. 23, 1989 [JP] Japan .................. 1-276593
Oct. 23, 1989 [JP] Japan .................. 1-276594

[51] Int. Cl.[6] .................. C07C 321/20; C07C 329/06
[52] U.S. Cl. ........................... 558/248; 564/240
[58] Field of Search .............. 558/248; 564/340, 342

[56] References Cited

U.S. PATENT DOCUMENTS 4,622,322 11/1986 Renfroe ................. 514/222
5,022,915 6/1991 Prisbylla ................. 71/92

FOREIGN PATENT DOCUMENTS 0354766 2/1990 European Pat. Off. .
60-72808 4/1985 Japan .

OTHER PUBLICATIONS

Takahashi et al., Journal of Heterocyclic Chemistry, vol., 23, pp. 77–80 (1986).
Bredereck et al., Chem Ber. 97, 3397 (1964).
Zumach et al., Angew Chem. Internat. Edit, 9, 54 (1970).
Becker et al., J. Org. Chem., 28, 1896 (1963).
Truce et al., J. Am. Chem. Soc., 77, 5063 (1955).

*Primary Examiner*—Richard L. Raymond
*Attorney, Agent, or Firm*—Sughrue, Mion, Zinn, Macpeak & Seas

[57] ABSTRACT

A compound of the formula (I):

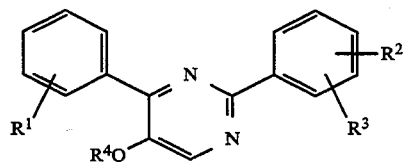

wherein $R^1$ represents a hydrogen atom, or a halogen atom, a ($C_1$ to $C_3$)-alkyl group, a halo-($C_1$ to $C_3$)-alkyl group, a ($C_1$ to $C_6$)-alkoxy group, a ($C_2$ to $C_6$)-alkynyloxy group, a ($C_2$ to $C_6$)-alkenyloxy group, a halo-($C_2$ to $C_6$)-alkynyloxy group, a halo-($C_2$ to $C_6$)-alkenyloxy group, a ($C_1$ to $C_2$)-alkylthio group, a halo-($C_1$ to $C_6$)-alkoxy group, a halo-($C_1$ to $C_2$)-alkylthio group, a phenoxy group, a ($C_1$ to $C_3$)-alkylcarboxy group, a halo-($C_1$ to $C_3$)-alkylcarboxy group, a ($C_1$ to $C_2$)-alkoxy-($C_1$ to $C_2$)-alkoxy group, a halo-($C_1$ to $C_2$)-alkoxy-halo-($C_2$ to $C_3$)-alkoxy group, a ($C_1$ to $C_3$)-alkylsulfonyloxy group, a halo-($C_1$ to $C_3$)-alkylsulfonyloxy group, a cyano group, a ($C_1$ to $C_3$)-alkoxycarbonyl group or an aminomethyl group, at the ortho or meta position; $R^2$ and $R^3$, which may be either the same or different, each represents a hydrogen atom, a halogen atom, a ($C_1$ to $C_2$)-alkyl group, a halo-($C_1$ to $C_2$)-alkyl group, a ($C_1$ to $C_2$)-alkoxy group, a nitro group, a ($C_1$ to $C_2$)-alkylthio group, a halo-($C_1$ to $C_2$)-alkylthio group or a halo-($C_1$ to $C_2$)-alkoxy group; and $R^4$ represents a ($C_1$ to $C_2$)-alkyl group, provided that both $R^1$ and $R^2$ are not a hydrogen atom at the same time and that both of $R^2$ and $R^3$, if each representing a substituent other than a hydrogen atom, are not at the ortho position for the pyrimidine ring at the same time. The compound is used as herbicides.

2 Claims, No Drawings

5-SUBSTITUTED-2,4-DIPHENYLPYRIMIDINE DERIVATIVES, THEIR PRODUCTION AND USE

This is a Divisional application of application Ser. No. 08/106,604, filed Aug. 16, 1993, now U.S. Pat. No. 5,349,108, which is a Divisional application of application Ser. No. 07/972,806, filed Nov. 6, 1992, now U.S. Pat. No. 5,270,467, which is a Divisional application of application Ser. No. 07/809,649, filed Dec. 17, 1991, now U.S. Pat. No. 5,190,575, which is a Continuation of application Ser. No. 07/602,833, filed Oct. 23, 1990, which is a Continuation-in-Part of (1) application Ser. No. 07/544,089, filed Jun. 22, 1990, now abandonned, which is a Continuation of application Ser. No. 07/391,016, filed Aug. 9, 1989, now abandoned, and (2) application Ser. No. 07/508,446 filed Apr. 13, 1990, now abandoned, which is a Divisional application of application Ser. No. 07/391,016, filed Aug. 9, 1989, now abandoned.

The present invention relates to 5-substituted-2,4-diphenylpyrimidine derivatives, their production and use, and to novel intermediates useful for producing such derivatives and their production and use. More particularly, it relates to novel 5-substituted-2,4-diphenylpyrimidine derivatives, a process for producing them, their use as herbicides, intermediates useful for producing them and a process for producing such intermediates.

There have been used a number of herbicides. However, since they are insufficient for herbicidal effects, and also poor in the selectivity between crops and weeds, they do not always satisfy.

The present inventors have made extensive and intensive studies to develop excellent herbicides, and consequently found that the following compound is good in the herbicidal activity as well as in the selectivity between crops and weeds. The present invention is based on this finding.

Namely, the compound of the present invention has the following structural formula (I);

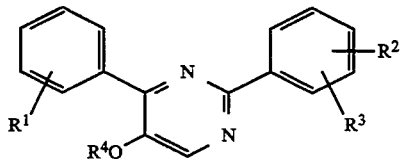

(I)

wherein $R^1$ represents a hydrogen atom, or a halogen atom, a ($C_1$ to $C_3$)-alkyl group, a halo-($C_1$ to $C_3$)-alkyl group, a ($C_1$ to $C_6$)-alkoxy group, a ($C_2$ to $C_6$)-alkynyloxy group, a ($C_2$ to $C_6$)-alkenyloxy group, a halo-($C_2$ to $C_6$)-alkynyloxy group, a halo-($C_2$ to $C_6$)-alkenyloxy group, a ($C_1$ to $C_2$)-alkylthio group, a halo-($C_1$ to $C_6$)-alkoxy group, a halo-($C_1$ to $C_2$)-alkylthio group, a phenoxy group, a ($C_1$ to $C_3$)-alkylcarboxy group, a halo-($C_1$ to $C_3$)-alkylcarboxy group, a ($C_1$ to $C_2$)-alkoxy-($C_1$ to $C_2$)-alkoxy group, a halo-($C_1$ to $C_2$)-alkoxy-halo-($C_2$ to $C_3$)-alkoxy group, a ($C_1$ to $C_3$)-alkylsulfonyloxy group, a halo-($C_1$ to $C_3$)-alkylsulfonyloxy group, a cyano group, a ($C_1$ to $C_3$)-alkoxycarbonyl group or an aminomethyl group, at the ortho or meta position; $R^2$ and $R^3$, which may be either the same or different, each represents a hydrogen atom, a halogen atom, a ($C_1$ to $C_2$)-alkyl group, a halo-($C_1$ to $C_2$)-alkyl group, a ($C_1$ to $C_2$)-alkoxy group, a nitro group, a ($C_1$ to $C_2$)-alkylthio group, a halo-($C_1$ to $C_2$)-alkylthio group or a halo-($C_1$ to $C_2$)-alkoxy group; and $R^4$ represents a ($C_1$ to $C_2$)-alkyl group, provided that $R^1$, $R^2$ and $R^3$ are not a hydrogen atom at the same time and that both of $R^2$ and $R^3$, if each representing a substituent other than a hydrogen atom, are not at the ortho position for the pyrimidine ring at the same time.

Hitherto, J. Heterocyclic Chem., 23, 77 (1986) discloses 2,4-diphenyl-5-methanesulfonylpyrimidine, etc. similar to the compound of the present invention. However, in this paper, no mention is made of the biological activity of the compounds. Further, the paper does not disclose at all the chemical structure and biological activity of 5-substituted-2,4-diphenylpyrimidine derivatives of the present invention.

The compound of the present invention has an excellent herbicidal activity, and is good in the selectivity between crops and weeds. Namely, the compound of the present invention has a good herbicidal activity on a number of undesired weeds, which will cause a problem, by the foliar treatment as well as the soil treatment in up land fields. Examples of these weeds include broad-leaved weeds such as common chickweed (*Stellaria media*), radish (*Raphanus sativus*), wild mustard (*Sinapis arvensis*), velvetleaf (*Abutilon theophrasti*), prickly sida (*Sida spinosa*), field pansy (*Viola arvensis*), redroot pigweed (*Amaranthus retroflexus*), catchweed bedstraw (*Galium aparine*), ivyleaf morningglory (*Ipomoea hederacea*), tall morningglory (*Pharbitis purpurea*), black nightshade (*Solanum nigrum*), and persian speedwell (*Veronica persica*); graminaceous weeds such as Japanese millet (*Echinochloa frumentacea*), annual bluegrass (*Poa annua*), barnyardgrass (*Echinochloa crus-galli*), green foxtail (*Setaria viridis*), large crabgrass (*Digitaria sanguinalis*), oats (*Arena sativa*), blackgrass (*Alopecurus myosuroides*), and wild oats (*Arena fatua*); and Cyperaceous weeds such as hardstem bulrush (*Scirpus juncoides*) and water nutgrass (*Cyperus serotinus*). In addition, the compound of the present invention does not exert undesired phytotoxicity to main crops such as wheat, barley, rice plant, soybean, cotton, and corn.

Further, the compound of the present invention has a herbicidal activity on a variety of weeds in paddy fields, for example, graminaceous weeds such as barnyardgrass (*Echinochloa oryzoides*), and does not exert undesired phytotoxicity on rice plant.

In the compound of the present invention, it is preferable that $R^3$ is a hydrogen atom. It is also preferable that $R^1$ is a hydrogen atom, or a halogen atom, a ($C_1$ to $C_3$)-alkyl group, a halo-($C_1$ to $C_3$)-alkyl group, a ($C_1$ to $C_6$)-alkoxy group, a ($C_2$ to $C_6$)-alkynyloxy group, a ($C_2$ to $C_6$)-alkenyloxy group, a halo-($C_2$ to $C_6$)-alkynyloxy group, a halo-($C_2$ to $C_6$)-alkenyloxy group, a ($C_1$ to $C_2$)-alkylthio group, a halo-($C_1$ to $C_6$)-alkoxy group, a halo-($C_1$ to $C_2$)-alkylthio group, a phenoxy group, a ($C_1$ to $C_3$)-alkylcarboxy group, a halo-($C_1$ to $C_3$)-alkylcarboxy group, a ($C_1$ to $C_2$)-alkoxy-($C_1$ to $C_2$)-alkoxy group, a halo-($C_1$ to $C_2$)-alkoxy-halo-($C_2$ to $C_3$)-alkoxy group, a ($C_1$ to $C_3$)-alkylsulfonyloxy group, a halo-($C_1$ to $C_3$)-alkylsulfonyloxy group or a cyano group, at the meta position; and $R^2$ and $R^3$, which may be either the same or different, each is a hydrogen atom, or a halogen atom, a ($C_1$ to $C_2$)-alkyl group, a halo-($C_1$ to $C_2$)-alkyl group or a ($C_1$ to $C_2$)-alkoxy group, at the meta or para position. Among the above compounds, preferred are those that $R^1$ and $R^2$ are as described above and $R^3$ is a hydrogen atom.

More preferably, $R^1$ is a hydrogen atom, or a halogen atom, a trifluoromethyl group or a trihalomethoxy group, at the meta position; $R^2$ and $R^3$, which may be either the same or different, each is a hydrogen atom, or a halogen atom or a trifluoromethyl group, at the meta or para position; and $R^4$ is a methyl group. Among the above compounds, preferred are those that $R^1$ is as described above, $R^2$ is a hydrogen atom, or a halogen atom or a trifluoromethyl group, at the para position, and $R^3$ is a hydrogen atom. Further more preferably, $R^1$ is a trifluoromethyl group or a trifluoromethoxy group, at the meta position; $R^2$ and $R^3$, which may be either the same or different, each is a fluorine atom, a chlorine atom or a trifluoromethyl group, at the meta or para position; and $R^4$ is a methyl group. Most preferably, $R^1$ is a trifluoromethyl group or a trifluoromethoxy group, at the meta position; $R^2$ is a fluorine atom, a chlorine atom or a trifluoromethyl group, at the para position; $R^3$ is a hydrogen atom; and $R^4$ is a methyl group.

It is also preferable that $R^2$ and $R^3$, which may be either the same or different, each is a halogen atom or a halo-$(C_1$ to $C_2)$-alkyl group, more preferably, each is a halogen atom or a trifluoromethyl group at the meta or para position.

The particularly preferred compounds of the present invention include 2-(4-fluorophenyl)-4-(3-trifluoromethylphenyl)-5-methoxypyrimidine; 2-(4-trifluoromethylphenyl)-4-(3-trifluoromethoxyphenyl)-5-methoxypyrimidine; and 2-(4-fluorophenyl)-4-(3-trifluoromethoxyphenyl)-5-methoxypyrimidine.

The compound (I) of the present invention can be produced through the following reaction scheme:

Reaction Scheme

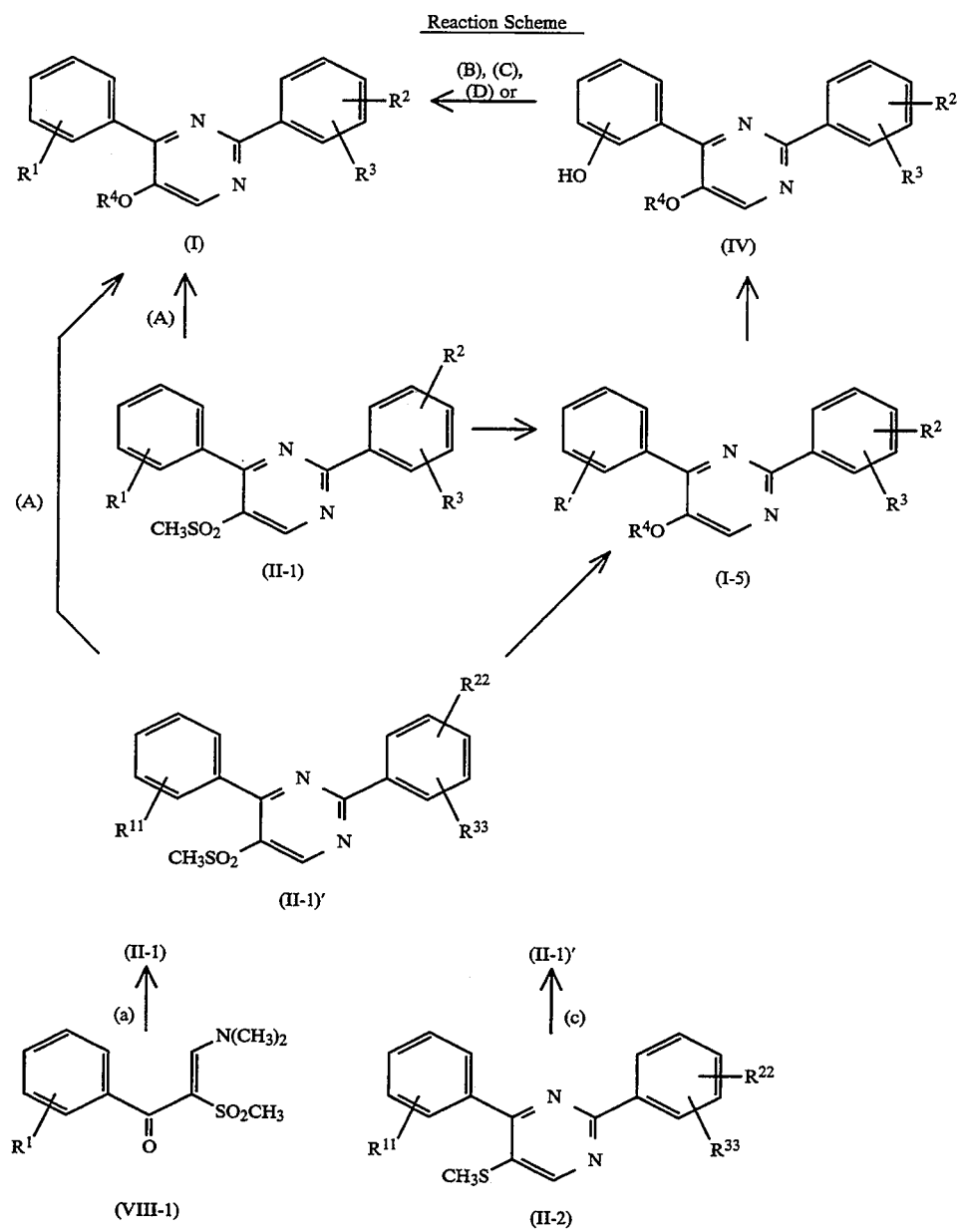

-continued
Reaction Scheme

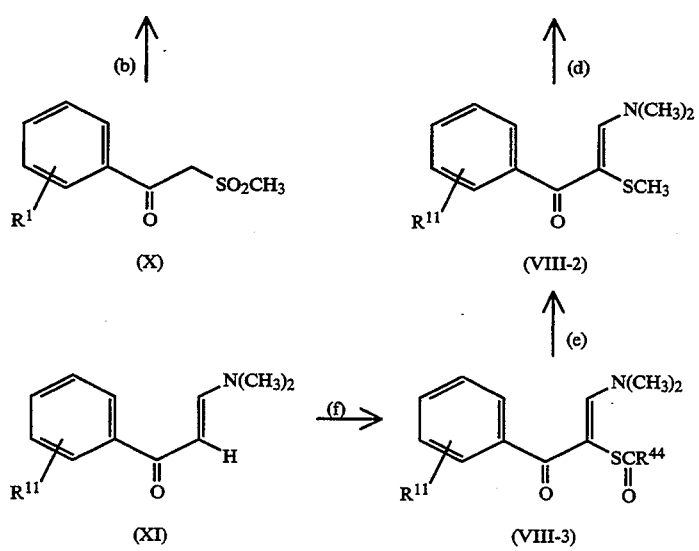

Procedure (A):

The compound (I) is prepared by reacting a compound of the formula (II-1):

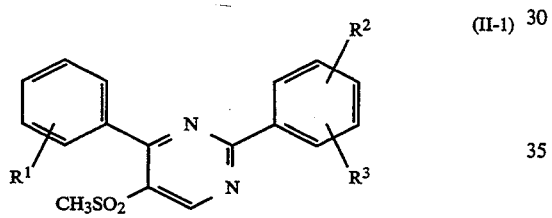

[wherein $R^1$, $R^2$ and $R^3$ are each as defined above] with a compound of the formula (III):

[wherein M is a metal atom (e.g., sodium), and $R^4$ is as defined above].

The reaction is usually carried out in an inert solvent at a temperature of about 20° to 100° C. for a period of about 0.5 to 5 hours.

Normally, the compound (III) is used in an amount of about 1 to 10 equivalents to one equivalent of the compound (II-1).

The solvent includes aliphatic hydrocarbons (e.g., hexane, heptane, ligroin, petroleum ether), aromatic hydrocarbons (e.g., benzene, toluene, xylene), ethers (e.g., diethyl ether, diisopropyl ether, dioxane, tetrahydrofuran, diethylene glycol dimethyl ether), alcohols (e.g., methanol, ethanol, isopropanol, t-butanol), esters (e.g., ethyl acetate, butyl acetate), acid amides (e.g., N,N-dimethylformamide, acetamide), sulfur compounds (e.g., dimethyl sulfoxide), and mixtures thereof.

The compound (III) includes alkali metal alkoxides (e.g., sodium methoxide, sodium ethoxide).

After completion of the reaction, the reaction mixture is subjected to the usual after-treatment such as extraction with organic solvents, concentration, etc., to obtain the compound (I) of the present invention, and if necessary, purified by chromatography, distillation, recrystallization, etc.

Procedure (B):

A compound of the formula (I-1):

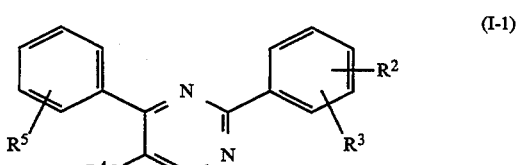

[wherein $R^5$ is a ($C_2$ to $C_6$)-alkoxy group, a halo-($C_1$ to $C_2$)-alkoxy-halo-($C_2$ to $C_3$)-alkoxy group or a halo-($C_2$ to $C_6$)-alkoxy group, at the ortho or meta position; and $R^2$, $R^3$ and $R^4$ are each as defined above] is prepared by reacting a compound of the formula (IV):

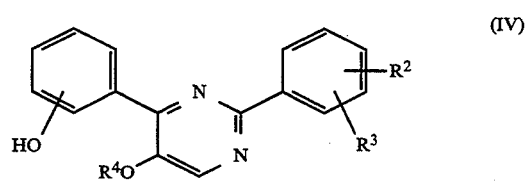

[wherein $R^2$, $R^3$ and $R^4$ are each as defined above; and the hydroxyl group of the phenol moiety bonded to the pyrimidine ring is positioned, at the ortho or meta position] with a ($C_2$ to $C_6$)-olefin which may be substituted with halogen or halo-($C_1$ to $C_2$)-alkoxy group.

The reaction is usually carried out in the presence of a base in an inert solvent at a temperature of 30° to 150° C. for a period of about 1 to 100 hours.

Normally, the olefin and the base are used respectively in amounts of about 5 to 30 equivalents and of about 1 to 10 equivalents to one equivalent of the compound (IV).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chlorobenzene, dichlorobenzene), ethers (e.g., diethyl ether, diisopropyl ether, dioxane, tetrahydrofuran, diethylene glycol dimethyl ether), nitriles (e.g., acetonitrile, isobutyronitrile), acid amides (e.g., N,N-dimethylformamide, acetamide), water, and mixtures thereof.

The base includes inorganic bases (e.g., sodium hydroxide, potassium hydroxide, sodium carbonate, potassium carbonate, sodium hydride), etc.

After completion of the reaction, the reaction mixture is subjected to the usual after-treatment such as extraction with organic solvents, concentration, etc., and if necessary, purified by chromatography, distillation, recrystallization, etc.

Procedure (C):

A compound of the formula (I-2):

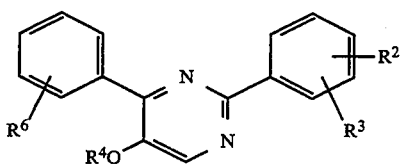

(I-2)

[wherein $R^6$ is a ($C_1$ to $C_3$)-alkylsulfonyloxy group or a halo-($C_1$ to $C_3$)-alkylsulfonyloxy group, at the ortho or meta position; and $R^2$, $R^3$ and $R^4$ are each as defined above] is prepared by reacting a compound of the formula (V):

$R^7$—Cl (V)

[wherein $R^7$ is a ($C_1$ to $C_3$)-alkylsulfonyl group which may be substituted with halogen] with the compound (IV).

The reaction is usually carried out with or without an inert solvent and in the presence of a base at a temperature of about 0° to 50° C. for a period of about 0.5 to 5 hours.

Normally, the compound (V) and the base are used respectively in amounts of about 1 to 2 equivalents and of about 1 to 5 equivalents to one equivalent of the compound (IV).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chloroform, carbon tetrachloride, dichloroethane, chlorobenzene, dichlorobenzene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), esters (e.g., ethyl formate, ethyl acetate, butyl acetate, diethyl carbonate), pyridine, acid amides (e.g., N,N-dimethylformamide, acetamide), water, and mixtures thereof.

The base includes organic bases (e.g., pyridine), etc.

After completion of the reaction, the reaction mixture is subjected to the usual after-treatment such as extraction with organic solvents, concentration, etc., and if necessary, purified by chromatography, distillation, recrystallization, etc.

Procedure (D):

A compound of the formula (I-3):

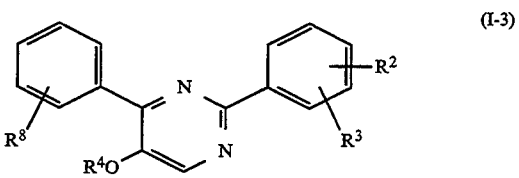

(I-3)

[wherein $R^8$ is a ($C_1$ to $C_6$)-alkoxy group which may contain an unsaturated bond, at the ortho or meta position; and $R^2$, $R^3$ and $R^4$ are each as defined above] is prepared by reacting a compound of the formula (VI):

$R^9$—X (VI)

[wherein $R^9$ is a ($C_1$ to $C_6$)-alkyl group, a ($C_2$ to $C_6$)-alkenyl group or a ($C_2$ to $C_6$)-alkynyl group; and X is a halogen atom] with the compound (IV).

The reaction is usually carried out in the presence of a base in an inert solvent at a temperature of 20° to 150° C. for a period of about 0.5 to 50 hours.

Normally, the compound (VI) and the base are used respectively in amounts of about 1 to 20 equivalents and of about 1 to 20 equivalents to one equivalent of the compound (IV).

The solvent includes aliphatic hydrocarbons (e.g., hexane, heptane, ligroin, petroleum ether), aromatic hydrocarbons (e.g., benzene, toluene, xylene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), esters (e.g., ethyl formate, ethyl acetate, butyl acetate, diethyl carbonate), nitriles (e.g., acetonitrile, isobutyronitrile), acid amides (e.g., N,N-dimethylformamide, acetamide), and water.

The base includes inorganic bases (e.g., sodium hydroxide, potassium hydroxide, sodium carbonate, potassium carbonate, sodium hydride), etc.

After completion of the reaction, the reaction mixture is subjected to the usual after-treatment such as extraction with organic solvents, concentration, etc., and if necessary, purified by chromatography, distillation, recrystallization, etc.

Procedure (E):

A compound of the formula (I-4):

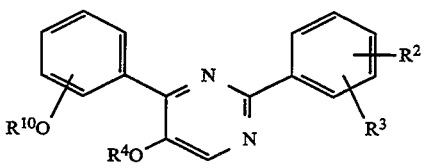

(I-4)

[wherein $R^{10}$ is a ($C_1$ to $C_3$)-acyl group which may be substituted with a halogen atom; and $R^2$, $R^3$ and $R^4$ are each as defined above] is prepared by reacting a compound of the formula (VII):

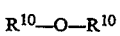

$R^{10}$—O—$R^{10}$ (VII)

[wherein $R^{10}$ is as defined above] with the compound (IV).

The reaction is usually carried out with or without an inert solvent and in the presence of an acid catalyst at a temperature of about 0° to 100° C. for a period of about 0.5 to 30 hours.

Normally, the compound (VII) is used in an amount of about 1 to 3 equivalents to one equivalent of the compound (IV).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chloroform, carbon tetrachloride, dichloroethane, chlorobenzene, dichlorobenzene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), acid amides (e.g, N,N,-dimethylformamide, acetamide), water, and mixtures thereof.

The acid catalyst includes organic acids (e.g., acetic acid), inorganic acids (e.g., hydrochloric acid, sulfuric acid), etc.

After completion of the reaction, the reaction mixture is subjected to the usual after-treatment such as extraction with organic solvents, concentration, etc., and if necessary, purified by chromatography, distillation, recrystallization, etc.

Table 1 illustrates examples of the compound (I) of the present invention which can be produced by the procedures (A)~(E).

TABLE 1

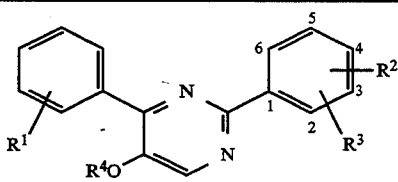

| $R^1$ | $R^2$ | $R^3$ | $R^4$ |
|---|---|---|---|
| H | 4-Cl | H | $CH_3$ |
| H | 4-Br | H | $CH_3$ |
| H | $4-CF_3$ | H | $CH_3$ |
| H | $4-NO_2$ | H | $CH_3$ |
| m-F | H | H | $CH_3$ |
| m-F | $4-CH_3$ | H | $CH_3$ |
| m-F | 4-F | H | $CH_3$ |
| m-F | $4-CF_3$ | H | $CH_3$ |
| m-F | 4-Cl | H | $CH_3$ |
| m-F | 4-Br | H | $CH_3$ |
| m-F | 4-F | H | $C_2H_5$ |
| m-Cl | 4-F | H | $CH_3$ |
| m-Cl | H | H | $CH_3$ |
| m-Cl | 4-Cl | H | $CH_3$ |
| m-Cl | $4-CF_3$ | H | $CH_3$ |
| m-Br | H | H | $CH_3$ |
| m-Br | 4-Cl | H | $CH_3$ |
| m-Br | 4-Br | H | $CH_3$ |
| m-Br | $4-CF_3$ | H | $CH_3$ |
| m-Br | $4-NO_2$ | H | $CH_3$ |
| m-Br | 4-F | H | $C_2H_5$ |
| o-Br | $4-CF_3$ | H | $CH_3$ |
| m-I | $4-CF_3$ | H | $CH_3$ |
| m-I | 4-F | H | $CH_3$ |
| m-I | 4-F | H | $C_2H_5$ |
| $m-CH_3$ | 4-F | H | $CH_3$ |
| $m-CH_3$ | $4-CF_3$ | H | $CH_3$ |
| $o-CH_3$ | $4-CF_3$ | H | $CH_3$ |
| $m-CF_3$ | H | H | $CH_3$ |
| $m-CF_3$ | $4-CH_3$ | H | $CH_3$ |
| $m-CF_3$ | 4-F | H | $CH_3$ |
| $m-CF_3$ | 4-Cl | H | $CH_3$ |
| $m-CF_3$ | 4-Br | H | $CH_3$ |
| $m-CF_3$ | $4-CF_3$ | H | $CH_3$ |
| $m-CF_3$ | $4-CH_3O$ | H | $CH_3$ |
| $m-CF_3$ | $3-CH_3O$ | H | $CH_3$ |
| $m-CF_3$ | 3-F | H | $CH_3$ |
| $m-CF_3$ | 2-F | H | $CH_3$ |

TABLE 1-continued

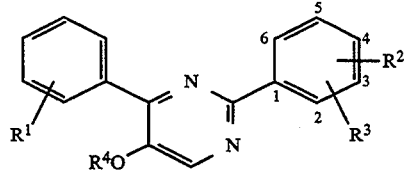

| $R^1$ | $R^2$ | $R^3$ | $R^4$ |
|---|---|---|---|
| $m-CF_3$ | 4-F | H | $C_2H_5$ |
| $m-CF_3$ | $4-CF_3$ | H | $C_2H_5$ |
| $m-CF_3$ | 4-Cl | H | $C_2H_5$ |
| $m-CF_3$ | $4-CH_3$ | H | $C_2H_5$ |
| $m-CF_3$ | H | H | $C_2H_5$ |
| $o-CF_3$ | $4-CF_3$ | H | $CH_3$ |
| $o-CF_3$ | 2-F | H | $CH_3$ |
| $m-CH_3O$ | 4-F | H | $CH_3$ |
| $m-CH_3O$ | $4-CF_3$ | H | $CH_3$ |
| $m-C_2H_5O$ | 4-F | H | $CH_3$ |
| $m-C_2H_5O$ | $4-CF_3$ | H | $CH_3$ |
| $m-(i)C_3H_7O$ | 4-F | H | $CH_3$ |
| $m-(sec)C_4H_9O$ | 4-F | H | $CH_3$ |
| $m-(sec)C_4H_9O$ | $4-CF_3$ | H | $CH_3$ |
| $m-CH_2=CHCH_2O$ | 4-F | H | $CH_3$ |
| $m-CH_2=CHCH_2O$ | $4-CF_3$ | H | $CH_3$ |
| $m-CH\equiv CCH_2O$ | 4-F | H | $CH_3$ |
| $m-CH\equiv CCH_2O$ | $4-CF_3$ | H | $CH_3$ |
| $m-CH_3S$ | 4-F | H | $CH_3$ |
| $m-CH_3S$ | $4-CF_3$ | H | $CH_3$ |
| $m-CF_3O$ | $4-CF_3$ | H | $CH_3$ |
| $m-CF_3O$ | 4-F | H | $CH_3$ |
| $m-CF_3O$ | 4-Cl | H | $CH_3$ |
| $m-CF_3O$ | 4-F | H | $C_2H_5$ |
| $m-CCl_3O$ | 4-F | H | $CH_3$ |
| $m-CCl_3O$ | $4-CF_3$ | H | $CH_3$ |
| $m-CF_2HO$ | 4-F | H | $CH_3$ |
| $m-CF_2HO$ | $4-CF_3$ | H | $CH_3$ |
| $m-CF_2ClO$ | 4-F | H | $CH_3$ |
| $m-CF_2ClO$ | $4-CF_3$ | H | $CH_3$ |
| $m-CF_3CF_2O$ | 4-F | H | $CH_3$ |
| $m-CF_3CF_2O$ | $4-CF_3$ | H | $CH_3$ |
| $m-CF_2HCF_2O$ | 4-F | H | $CH_3$ |
| $m-CF_2HCF_2O$ | $4-CF_3$ | H | $CH_3$ |
| $m-CCl_2HCF_2O$ | 4-F | H | $CH_3$ |
| $m-CCl_2HCF_2O$ | $4-CF_3$ | H | $CH_3$ |
| $m-CF_3S$ | 4-F | H | $CH_3$ |
| $m-CF_3S$ | $4-CF_3$ | H | $CH_3$ |
| $m-C_6H_5O$ | 4-F | H | $CH_3$ |
| $m-C_6H_5O$ | $4-CF_3$ | H | $CH_3$ |
| $m-CH_3CO_2$ | 4-F | H | $CH_3$ |
| $m-CH_3CO_2$ | $4-CF_3$ | H | $CH_3$ |
| $m-CClFHCF_2O$ | 4-F | H | $CH_3$ |
| $m-CClFHCF_2O$ | $4-CF_3$ | H | $CH_3$ |
| $m-CClFHCClFO$ | 4-F | H | $CH_3$ |
| $m-CClFHCClFO$ | $4-CF_3$ | H | $CH_3$ |
| $m-CF_3CO_2$ | 4-F | H | $CH_3$ |
| $m-CH_3OCH_2O$ | 4-F | H | $CH_3$ |
| $m-CH_3OCH_2O$ | $4-CF_3$ | H | $CH_3$ |
| $m-CH_3SO_3$ | 4-F | H | $CH_3$ |
| $m-CH_3SO_3$ | $4-CF_3$ | H | $CH_3$ |
| $m-CH_3CH_2SO_3$ | 4-F | H | $CH_3$ |
| $m-CH_3CH_2SO_3$ | $4-CF_3$ | H | $CH_3$ |
| $m-CF_3SO_3$ | 4-F | H | $CH_3$ |
| $m-CF_3SO_3$ | $4-CF_3$ | H | $CH_3$ |
| $m-CF_3CF_2SO_3$ | 4-F | H | $CH_3$ |
| $m-CF_3CF_2SO_3$ | $4-CF_3$ | H | $CH_3$ |
| $m-CF_3O$ | $4-CF_3O$ | H | $CH_3$ |
| $m-CF_3$ | $4-CF_3O$ | H | $CH_3$ |
| $m-CH_2NH_2$ | $4-CF_3$ | H | $CH_3$ |
| $m-CH_2NH_2$ | 4-F | H | $CH_3$ |
| $m-CF_3O$ | $4-SCH_3$ | H | $CH_3$ |
| $m-CF_3$ | $4-SCH_3$ | H | $CH_3$ |
| m-CN | $4-CF_3$ | H | $CH_3$ |
| m-CN | 4-F | H | $CH_3$ |
| $m-COOCH_3$ | 4-CF | H | $CH_3$ |
| $m-COOCH_3$ | 4-F | H | $CH_3$ |
| $m-CClF=CFO$ | 4-F | H | $CH_3$ |
| $m-CF_3O$ | $4-SCF_3$ | H | $CH_3$ |
| $m-CF_3$ | $4-SCF_3$ | H | $CH_3$ |
| H | 4-F | H | $CH_3$ |

TABLE 1-continued

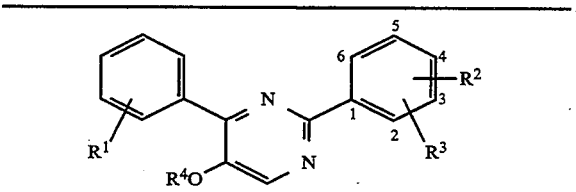

| R¹ | R² | R³ | R⁴ |
|---|---|---|---|
| H | 3-F | H | CH₃ |
| H | 3-CF₃ | H | CH₃ |
| H | 4-CH₃ | H | CH₃ |
| m-F | 3-F | H | CH₃ |
| m-F | 3-CF₃ | H | CH₃ |
| m-Cl | 3-F | H | CH₃ |
| m-Cl | 3-CF₃ | H | CH₃ |
| m-Cl | 4-CH₃ | H | CH₃ |
| m-CF₃ | 3-CF₃ | H | CH₃ |
| m-(i)C₃H₇O | H | H | CH₃ |
| m-(i)C₃H₇O | 4-CF₃ | H | CH₃ |
| m-(i)C₃H₇O | 3-F | H | CH₃ |
| m-(i)C₃H₇O | 3-CF₃ | H | CH₃ |
| m-(i)C₃H₇O | 4-Cl | H | CH₃ |
| m-(i)C₃H₇O | 4-CH₃ | H | CH₃ |
| m-(sec)C₄H₉O | H | H | CH₃ |
| m-(sec)C₄H₉O | 3-F | H | CH₃ |
| m-(sec)C₄H₉O | 3-CF₃ | H | CH₃ |
| m-(sec)C₄H₉O | 4-Cl | H | CH₃ |
| m-(sec)C₄H₉O | 4-CH₃ | H | CH₃ |
| m-CF₃O | H | H | CH₃ |
| m-CF₃O | 3-F | H | CH₃ |
| m-CF₃O | 3-CF₃ | H | CH₃ |
| m-CF₃O | 4-CH₃ | H | CH₃ |
| o-CF₃ | H | H | CH₃ |
| o-CF₃ | 4-F | H | CH₃ |
| o-CF₃ | 3-F | H | CH₃ |
| o-CF₃ | 3-CF₃ | H | CH₃ |
| o-CF₃ | 4-Cl | H | CH₃ |
| o-CF₃ | 4-CH₃ | H | CH₃ |
| H | 2-F | 4-Cl | CH₃ |
| H | 3-F | 4-Cl | CH₃ |
| H | 2-F | 4-Br | CH₃ |
| H | 3-F | 4-F | CH₃ |
| H | 2-F | 4-CF₃ | CH₃ |
| H | 3-F | 4-CF₃ | CH₃ |
| m-F | 2-F | 4-F | CH₃ |
| m-F | 3-F | 4-F | CH₃ |
| m-F | 2-F | 4-CF₃ | CH₃ |
| m-F | 3-F | 4-CF₃ | CH₃ |
| m-F | 2-F | 4-Cl | CH₃ |
| m-F | 3-F | 4-Cl | CH₃ |
| m-F | 2-F | 4-Br | CH₃ |
| m-F | 3-F | 4-Br | CH₃ |
| m-F | 2-F | 4-F | C₂H₅ |
| m-F | 3-F | 4-F | C₂H₅ |
| m-Cl | 2-F | 4-F | CH₃ |
| m-Cl | 3-F | 4-F | CH₃ |
| m-Cl | 2-F | 4-Cl | CH₃ |
| m-Cl | 3-F | 4-Cl | CH₃ |
| m-Cl | 2-F | 4-CF₃ | CH₃ |
| m-Cl | 3-F | 4-CF₃ | CH₃ |
| o-Br | 2-F | 4-CF₃ | CH₃ |
| o-Br | 3-F | 4-CF₃ | CH₃ |
| m-I | 2-F | 4-CF₃ | CH₃ |
| m-I | 3-F | 4-CF₃ | CH₃ |
| m-I | 2-F | 4-F | CH₃ |
| m-I | 3-F | 4-F | CH₃ |
| m-I | 2-F | 4-F | C₂H₅ |
| m-I | 3-F | 4-F | C₂H₅ |
| m-CH₃ | 2-F | 4-F | CH₃ |
| m-CH₃ | 3-F | 4-F | CH₃ |
| m-CH₃ | 2-F | 4-CF₃ | CH₃ |
| m-CH₃ | 3-F | 4-CF₃ | CH₃ |
| o-CH₃ | 2-F | 4-CF₃ | CH₃ |
| o-CH₃ | 3-F | 4-CF₃ | CH₃ |
| m-CF₃ | 3-F | 5-F | CH₃ |
| m-CF₃ | 2-F | 4-F | CH₃ |
| m-CF₃ | 3-F | 4-F | CH₃ |
| m-CF₃ | 2-F | 4-Cl | CH₃ |
| m-CF₃ | 3-F | 4-Cl | CH₃ |

TABLE 1-continued

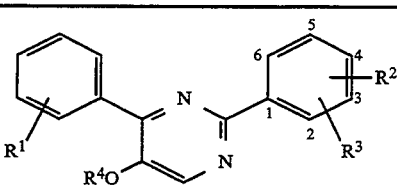

| R¹ | R² | R³ | R⁴ |
|---|---|---|---|
| m-CF₃ | 2-F | 4-CF₃ | CH₃ |
| m-CF₃ | 3-F | 4-CF₃ | CH₃ |
| m-CF₃ | 3-CF₃ | 4-F | CH₃ |
| m-CF₃ | 3-Cl | 4-F | CH₃ |
| m-CF₃ | 2-F | 4-CF₃ | C₂H₅ |
| m-CF₃ | 3-F | 4-CF₃ | C₂H₅ |
| m-CF₃ | 2-F | 4-Cl | C₂H₅ |
| m-CF₃ | 3-F | 4-Cl | C₂H₅ |
| m-CH₃O | 2-F | 4-F | CH₃ |
| m-CH₃O | 3-F | 4-F | CH₃ |
| m-CH₃O | 2-F | 4-CF₃ | CH₃ |
| m-CH₃O | 3-F | 4-CF₃ | CH₃ |
| m-C₂H₅O | 2-F | 4-F | CH₃ |
| m-C₂H₅O | 3-F | 4-F | CH₃ |
| m-C₂H₅O | 2-F | 4-CF | CH₃ |
| m-C₂H₅O | 3-F | 4-CF₃ | CH₃ |
| m-(i)C₃H₇O | 2-F | 4-F | CH₃ |
| m-(i)C₃H₇O | 3-F | 4-F | CH₃ |
| m-(sec)C₄H₉O | 2-F | 4-F | CH₃ |
| m-(sec)C₄H₉O | 3-F | 4-F | CH₃ |
| m-(sec)C₄H₉O | 2-F | 4-CF₃ | CH₃ |
| m-(sec)C₄H₉O | 3-F | 4-CF₃ | CH₃ |
| m-CH₂=CHCH₂O | 2-F | 4-F | CH₃ |
| m-CH₂=CHCH₂O | 3-F | 4-F | CH₃ |
| m-CH₂=CHCH₂O | 2-F | 4-CF₃ | CH₃ |
| m-CH₂=CHCH₂O | 3-F | 4-CF₃ | CH₃ |
| m-CH≡CCH₂O | 2-F | 4-F | CH₃ |
| m-CH≡CCH₂O | 3-F | 4-F | CH₃ |
| m-CH≡CCH₂O | 2-F | 4-CF₃ | CH₃ |
| m-CH≡CCH₂O | 3-F | 4-CF₃ | CH₃ |
| m-CH₃S | 2-F | 4-F | CH₃ |
| m-CH₃S | 3-F | 4-F | CH₃ |
| m-CH₃S | 2-F | 4-CF₃ | CH₃ |
| m-CH₃S | 3-F | 4-CF₃ | CH₃ |
| m-CF₃O | 2-F | 4-CF₃ | CH₃ |
| m-CF₃O | 3-F | 4-CF₃ | CH₃ |
| m-CF₃O | 3-CF₃ | 4-F | CH₃ |
| m-CF₃O | 2-F | 4-F | CH₃ |
| m-CF₃O | 3-F | 4-F | CH₃ |
| m-CF₃O | 2-F | 4-Cl | CH₃ |
| m-CF₃O | 3-F | 4-Cl | CH₃ |
| m-CF₃O | 3-Cl | 4-F | CH₃ |
| m-CF₃O | 2-F | 4-F | C₂H₅ |
| m-CF₃O | 3-F | 4-F | C₂H₅ |
| m-CCl₃O | 2-F | 4-F | CH₃ |
| m-CCl₃O | 3-F | 4-F | CH₃ |
| m-CCl₃O | 2-F | 4-CF₃ | CH₃ |
| m-CCl₃O | 3-F | 4-CF₃ | CH₃ |
| m-CF₂HO | 2-F | 4-F | CH₃ |
| m-CF₂HO | 3-F | 4-F | CH₃ |
| m-CF₂HO | 2-F | 4-CF₃ | CH₃ |
| m-CF₂HO | 3-F | 4-CF₃ | CH₃ |
| m-CF₂ClO | 2-F | 4-F | CH₃ |
| m-CF₂ClO | 3-F | 4-F | CH₃ |
| m-CF₂ClO | 2-F | 4-CF₃ | CH₃ |
| m-CF₂ClO | 3-F | 4-CF₃ | CH₃ |
| m-CF₃CF₂O | 2-F | 4-F | CH₃ |
| m-CF₃CF₂O | 3-F | 4-F | CH₃ |
| m-CF₃CF₂O | 2-F | 4-CF₃ | CH₃ |
| m-CF₃CF₂O | 3-F | 4-CF₃ | CH₃ |
| m-CF₂HCF₂O | 2-F | 4-F | CH₃ |
| m-CF₂HCF₂O | 3-F | 4-F | CH₃ |
| m-CF₂HCF₂O | 2-F | 4-CF₃ | CH₃ |
| m-CF₂HCF₂O | 3-F | 4-CF₃ | CH₃ |
| m-CCl₂HCF₂O | 2-F | 4-F | CH₃ |
| m-CCl₂HCF₂O | 3-F | 4-F | CH₃ |
| m-CCl₂HCF₂O | 2-F | 4-CF₃ | CH₃ |
| m-CCl₂HCF₂O | 3-F | 4-CF₃ | CH₃ |
| m-CF₂BrO | 2-F | 4-F | CH₃ |
| m-CF₂BrO | 3-F | 4-F | CH₃ |
| m-CF₂BrO | 2-F | 4-CF₃ | CH₃ |

TABLE 1-continued

[Structure: diphenyl pyrimidine compound with substituents R¹ (ortho phenyl), R² (position 4), R³ (position 2), R⁴O (on pyrimidine position 5); phenyl positions labeled 1,2,3,4,5,6]

| R¹ | R² | R³ | R⁴ |
|---|---|---|---|
| m-CF$_2$BrO | 3-F | 4-CF$_3$ | CH$_3$ |
| m-CF$_3$S | 2-F | 4-F | CH$_3$ |
| m-CF$_3$S | 3-F | 4-F | CH$_3$ |
| m-CF$_3$S | 2-F | 4-CF$_3$ | CH$_3$ |
| m-CF$_3$S | 3-F | 4-CF$_3$ | CH$_3$ |
| m-C$_6$H$_5$O | 2-F | 4-F | CH$_3$ |
| m-C$_6$H$_5$O | 3-F | 4-F | CH$_3$ |
| m-C$_6$H$_5$O | 2-F | 4-CF$_3$ | CH$_3$ |
| m-C$_6$H$_5$O | 3-F | 4-CF$_3$ | CH$_3$ |
| m-CH$_3$CO$_2$ | 2-F | 4-F | CH$_3$ |
| m-CH$_3$CO$_2$ | 3-F | 4-F | CH$_3$ |
| m-CH$_3$CO$_2$ | 2-F | 4-CF$_3$ | CH$_3$ |
| m-CH$_3$CO$_2$ | 3-F | 4-CF$_3$ | CH$_3$ |
| m-CClFHCF$_2$O | 2-F | 4-F | CH$_3$ |
| m-CClFHCF$_2$O | 3-F | 4-F | CH$_3$ |
| m-CClFHCF$_2$O | 2-F | 4-CF$_3$ | CH$_3$ |
| m-CClFHCF$_2$O | 3-F | 4-CF$_3$ | CH$_3$ |
| m-CClFHCClFO | 2-F | 4-F | CH$_3$ |
| m-CClFHCClFO | 3-F | 4-F | CH$_3$ |
| m-CClFHCClFO | 2-F | 4-CF$_3$ | CH$_3$ |
| m-CClFHCClFO | 3-F | 4-CF$_3$ | CH$_3$ |
| m-CF$_3$CO$_2$ | 2-F | 4-F | CH$_3$ |
| m-CF$_3$CO$_2$ | 3-F | 4-F | CH$_3$ |
| m-CH$_3$OCH$_2$O | 2-F | 4-F | CH$_3$ |
| m-CH$_3$OCH$_2$O | 3-F | 4-F | CH$_3$ |
| m-CH$_3$OCH$_2$O | 2-F | 4-CF | CH$_3$ |
| m-CH$_3$OCH$_2$O | 3-F | 4-CF$_3$ | CH$_3$ |
| m-CH$_3$SO$_3$ | 2-F | 4-F | CH$_3$ |
| m-CH$_3$SO$_3$ | 3-F | 4-F | CH$_3$ |
| m-CH$_3$SO$_3$ | 2-F | 4-CF$_3$ | CH$_3$ |
| m-CH$_3$SO$_3$ | 3-F | 4-CF$_3$ | CH$_3$ |
| m-C$_2$H$_5$SO$_3$ | 2-F | 4-F | CH$_3$ |
| m-C$_2$H$_5$SO$_3$ | 3-F | 4-F | CH$_3$ |
| m-C$_2$H$_5$SO$_3$ | 2-F | 4-CF$_3$ | CH$_3$ |
| m-C$_2$H$_5$SO$_3$ | 3-F | 4-CF$_3$ | CH$_3$ |
| m-CF$_3$SO$_3$ | 2-F | 4-F | CH$_3$ |
| m-CF$_3$SO$_3$ | 3-F | 4-F | CH$_3$ |
| m-CF$_3$SO$_3$ | 2-F | 4-CF$_3$ | CH$_3$ |
| m-CF$_3$SO$_3$ | 3-F | 4-CF$_3$ | CH$_3$ |
| m-CF$_3$CF$_2$SO$_3$ | 2-F | 4-F | CH$_3$ |
| m-CF$_3$CF$_2$SO$_3$ | 3-F | 4-F | CH$_3$ |
| m-CF$_3$CF$_2$SO$_3$ | 2-F | 4-CF$_3$ | CH$_3$ |
| m-CF$_3$CF$_2$SO$_3$ | 3-F | 4-CF$_3$ | CH$_3$ |
| m-CH$_2$NH$_2$ | 2-F | 4-F | CH$_3$ |
| m-CH$_2$NH$_2$ | 3-F | 4-F | CH$_3$ |
| m-CH$_2$NH$_2$ | 2-F | 4-CF$_3$ | CH$_3$ |
| m-CH$_2$NH$_2$ | 3-F | 4-CF$_3$ | CH$_3$ |
| m-CN | 2-F | 4-F | CH$_3$ |
| m-CN | 3-F | 4-F | CH$_3$ |
| m-CN | 2-F | 4-CF$_3$ | CH$_3$ |
| m-CN | 3-F | 4-CF$_3$ | CH$_3$ |
| m-COOCH$_3$ | 2-F | 4-F | CH$_3$ |
| m-COOCH$_3$ | 3-F | 4-F | CH$_3$ |
| m-COOCH$_3$ | 2-F | 4-CF$_3$ | CH$_3$ |
| m-COOCH$_3$ | 3-F | 4-CF$_3$ | CH$_3$ |
| m-CF$_2$BrO | 4-F | H | CH$_3$ |
| m-CF$_2$BrO | 4-CF$_3$ | H | CH$_3$ |
| m-CF$_2$BrCF$_2$O | 4-F | H | CH$_3$ |
| m-CF$_2$BrCF$_2$O | 4-CF$_3$ | H | CH$_3$ |
| m-CF$_3$OCFHCF$_2$O | 4-F | H | CH$_3$ |
| m-CF$_3$OCFHCF$_2$O | 4-CF$_3$ | H | CH$_3$ |

The present invention will be illustrated in more detail by the following examples, but the present invention is not construed as being limited thereto.

First, Production Examples of the present invention are shown below.

PRODUCTION EXAMPLE 1

2 g of 2-(4-fluorophenyl)-4-(3-trifluoromethylphenyl)-5-methanesulfonylpyrimidine, 0.3 g of sodium methoxide and 20 ml of methanol were added to 120 ml of ethylene glycol dimethyl ether, and the resulting mixture was heated under reflux for 5 hours. The solvent was distilled away under reduced pressure. The residue was washed with water, and then dried to obtain 1.5 g of 2-(4-fluorophenyl)-4-(3-trifluoromethylphenyl)-5-methoxypyrimidine (Compound 18).

PRODUCTION EXAMPLE 2

1.5 g of 2-(4-fluorophenyl)-4-(3-hydroxyphenyl)-5-methoxypyrimidine and 0.25 g of sodium hydride were added to 15 ml of N,N-dimethylformamide, and the resulting mixture was heated to 70° C. After adding 6.6 g of 1,1-dichloro-2,2-difluoroethylene thereto, the mixture was heated under reflux for 3 days. After completion of the reaction, ice-cold water was added to the mixture. Subsequently the mixture was extracted with ethyl acetate. The solvent was evaporated off, and the residue was purified by column chromatography on silica gel, thereby obtaining 1.0 g of 2-(4-fluorophenyl)-4-[3-(1',1'-difluoro-2',2'-di chloroethoxy)-phenyl]-5-methoxypyrimidine (Compound 53).

PRODUCTION EXAMPLE 3

1.2 g of 2-(4-fluorophenyl)-4-(3-hydroxyphenyl)-5-methoxypyrimidine and 0.57 g of methanesulfonyl chloride were added to 10 ml of pyridine, and the resulting mixture was stirred for 3 hours at room temperature. After completion of the reaction, ice-cold water was added to the mixture. Subsequently, the mixture was extracted with ethyl acetate. The solvent was evaporated off, and the residue was purified by column chromatography on silica gel, thereby obtaining 1.0 g 2-(4-fluorophenyl)-4-(3-methanesulfonyloxyphenyl)-5-methoxypyrimidine (Compound 54).

PRODUCTION EXAMPLE 4

1.2 g of 2-(4-fluorophenyl)-4-(3-hydroxyphenyl)-5-methoxypyrimidine, 5.5 g of potassium carbonate, and 5.5 g of 2-bromobutane were added to 200 ml of acetone, and the resulting mixture was heated under reflux for 2 days. The solvent was distilled away under reduced pressure. The residue was washed with water, and then purified by column chromatography on silica gel, thereby obtaining 1.0 g of 2-(4-fluorophenyl)-4-[3-sec-butoxyphenyl)-5-methoxypyrimidine (Compound 50).

PRODUCTION EXAMPLE 5

One drop of 96% sulfuric acid was added to a mixture of 1.2 g of 2-(4-fluorophenyl)-4-(3-hydroxyphenyl)-5-methoxypyrimidine and 0.5 g of acetic anhydride, and the resulting mixture was stirred for 20 hours at room temperature. After completion of the reaction, ice-cold water was added to mixture. Subsequently, the mixture was extracted with ethyl acetate. The solvent was evaporated off, and the residue was purified by column chromatography on silica gel thereby obtaining 1.0 g of 2-(4-fluorophenyl)-4-(3-acetoxyphenyl)-5-methoxypyrimidine (Compound 55).

PRODUCTION EXAMPLE 6

2.1 g of 2-(2,4-difluorophenyl)-4-(3-trifluoromethylphenyl)-5-methanesulfonylpyrimidine, 0.3 g of sodium methoxide and 20 ml of methanol were added to 120 ml of ethylene glycol dimethyl ether and the resulting mixture was heated under reflux for 5 hours. The solvent was distilled away under reduced pressure. The residue was washed with water and then dried to obtain 1.55 g of 2-(2,4-difluorophenyl)-4-(3-trifluoromethylphenyl)-5-methoxypyrimidine (Compound 77).

Table 2 illustrates part of the compounds of the present invention produced according to the above Production Examples.

TABLE 2

| Compound No. | $R^1$ | $R^2$ | $R^3$ | $R^4$ | Melting Point (°C.) |
|---|---|---|---|---|---|
| 1 | m-Cl | 4-F | H | $CH_3$ | 126.0 |
| 2 | H | 4-Cl | H | $CH_3$ | 105.5 |
| 3 | H | 4-Br | H | $CH_3$ | 155.4 |
| 4 | H | 4-$CF_3$ | H | $CH_3$ | 84.4 |
| 5 | H | 4-$NO_2$ | H | $CH_3$ | 163.5 |
| 6 | m-Cl | H | H | $CH_3$ | 97.0 |
| 7 | m-Cl | 4-Cl | H | $CH_3$ | 143.0 |
| 8 | m-Cl | 4-$CF_3$ | H | $CH_3$ | 97.0 |
| 9 | m-Br | H | H | $CH_3$ | 103.2 |
| 10 | m-Br | 4-Cl | H | $CH_3$ | 153.3 |
| 11 | m-Br | 4-Br | H | $CH_3$ | 158.9 |
| 12 | m-Br | 4-$CF_3$ | H | $CH_3$ | 124.5 |
| 13 | m-Br | 4-$NO_2$ | H | $CH_3$ | 152.1 (dec) |
| 14 | o-Br | 4-$CF_3$ | H | $CH_3$ | 119.0 |
| 15 | o-$CH_3$ | 4-$CF_3$ | H | $CH_3$ | 103.4 |
| 16 | m-$CF_3$ | H | H | $CH_3$ | 92.6 |
| 17 | m-$CF_3$ | 4-$CH_3$ | H | $CH_3$ | 95.8 |
| 18 | m-$CF_3$ | 4-F | H | $CH_3$ | 98.9 |
| 19 | m-$CF_3$ | 4-Cl | H | $CH_3$ | 127.4 |
| 20 | m-$CF_3$ | 4-Br | H | $CH_3$ | 130.5 |
| 21 | m-$CF_3$ | 4-$CF_3$ | H | $CH_3$ | 108.3 |
| 22 | m-$CF_3$ | 4-$CH_3O$ | H | $CH_3$ | 104.3 |
| 23 | m-I | 4-$CF_3$ | H | $CH_3$ | 131.4 |
| 24 | m-F | H | H | $CH_3$ | 83.5 |
| 25 | m-F | 4-$CH_3$ | H | $CH_3$ | 72.5 |
| 26 | m-F | 4-F | H | $CH_3$ | 98.3 |
| 27 | m-F | 4-$CF_3$ | H | $CH_3$ | 101.3 |
| 28 | m-F | 4-Cl | H | $CH_3$ | 104.5 |
| 29 | m-F | 4-Br | H | $CH_3$ | 131.2 |
| 30 | o-$CF_3$ | 4-$CF_3$ | H | $CH_3$ | 142.5 |
| 31 | m-$CF_3O$ | 4-$CF_3$ | H | $CH_3$ | 94.6 |
| 32 | m-$CF_3O$ | 4-F | H | $CH_3$ | 73.9 |
| 33 | m-I | 4-F | H | $CH_3$ | 111.5 |
| 34 | m-$CF_3$ | 4-F | H | $C_2H_5$ | 90.6 |
| 35 | m-$CF_3$ | 4-$CF_3$ | H | $C_2H_5$ | 101.4 |
| 36 | m-$CF_3$ | 4-Cl | H | $C_2H_5$ | 103.0 |
| 37 | m-$CF_3$ | 4-$CH_3$ | H | $C_2H_5$ | 98.4 |
| 38 | m-$CF_3$ | H | H | $C_2H_5$ | 104.1 |
| 39 | m-Br | 4-F | H | $C_2H_5$ | 110.0 |
| 40 | m-F | 4-F | H | $C_2H_5$ | 111.9 |
| 41 | m-I | 4-F | H | $C_2H_5$ | 122.5 |
| 42 | m-$CF_3O$ | 4-F | H | $C_2H_5$ | 66.6 |
| 43 | m-$CH_3$ | 4-F | H | $CH_3$ | 106.7 |
| 44 | m-$C_2H_5O$ | 4-F | H | $CH_3$ | 86.1 |
| 45 | m-$CH_3OCH_2O$ | 4-F | H | $CH_3$ | 93.4 |
| 46 | m-$CH_3O$ | 4-F | H | $CH_3$ | 90.2 |
| 47 | m-(i)$C_3H_7O$ | 4-F | H | $CH_3$ | 78.2 |
| 48 | m-$CF_3O$ | 4-Cl | H | $CH_3$ | 95.3 |
| 49 | m-$CF_2HCF_2O$ | 4-F | H | $CH_3$ | 79.2 |
| 50 | m-(sec)$C_4H_9O$ | 4-F | H | $CH_3$ | 86.0 |
| 51 | m-$C_6H_5O$ | 4-F | H | $CH_3$ | 150.4 |
| 52 | m-$CF_3$ | 2-F | H | $CH_3$ | 67.8 |
| 53 | m-$CCl_2HCF_2O$ | 4-F | H | $CH_3$ | 75.5 |
| 54 | m-$CH_3SO_3$ | 4-F | H | $CH_3$ | 121.4 |
| 55 | m-$CH_3CO_2$ | 4-F | H | $CH_3$ | 113.6 |
| 56 | m-$CF_3CO_2$ | 4-F | H | $CH_3$ | 147.4 |
| 57 | m-$CF_3$ | 3-$CH_3O$ | H | $CH_3$ | 83.1 |
| 58 | m-$CF_3$ | 3-F | H | $CH_3$ | 60.0 |
| 59 | m-$CF_3SO_3$ | 4-F | H | $CH_3$ | 127.5 |
| 60 | m-$CH_3O$ | 4-$CF_3$ | H | $CH_3$ | 98.2 |
| 61 | m-$C_2H_5O$ | 4-$CF_3$ | H | $CH_3$ | 86.4 |
| 62 | m-$CH_3OCH_2O$ | 4-$CF_3$ | H | $CH_3$ | 79.3 |
| 63 | m-$C_6H_5O$ | 4-$CF_3$ | H | $CH_3$ | 132.2 |
| 64 | m-$CF_3$ | 3-$CF_3$ | H | $CH_3$ | 98.2 |
| 65 | m-$CF_3O$ | 3-F | H | $CH_3$ | 51.6 |
| 66 | m-$CF_3O$ | 3-$CF_3$ | H | $CH_3$ | 55.7 |
| 67 | m-$CH_2=CHCH_2O$ | 4-F | H | $CH_3$ | 1.6180 ($n_D^{25}$) |
| 68 | m-$CF_3$ | 3-Cl | H | $CH_3$ | 78.8 |
| 69 | m-$CF_2HO$ | 4-$CF_3$ | H | $CH_3$ | 93.4 |
| 70 | m-$CF_3O$ | 3-Cl | H | $CH_3$ | 77.8 |
| 71 | m-$CF_3$ | 4-$SCH_3$ | H | $CH_3$ | 121.1 |
| 72 | m-CN | 4-$CF_3$ | H | $CH_3$ | 131.7 |
| 73 | m-$CF_2HO$ | 4-F | H | $CH_3$ | 88.5 |

| Compound No. | $R^1$ | $R^2$ | $R^3$ | $R^4$ | $^1$H-NMR (δ value)* |
|---|---|---|---|---|---|
| 74 | m-$CF_3O$ | 2-F | 4-F | $CH_3$ | 8.40(s, 1H), 8.35~6.65(m, 7H), 3.95(s, 3H) |
| 75 | m-$CF_3O$ | 3-F | 4-F | $CH_3$ | 8.45~6.90(m, 8H), 4.0(s, 3H) |
| 76 | m-$CF_3O$ | 3-F | 5-F | $CH_3$ | 8.35(s, 1H), 8.20~6.50(m, 7H), 3.95(s, 3H) |
| 77 | m-$CF_3$ | 2-F | 4-F | $CH_3$ | 8.55~6.70(m, 8H), 4.05(s, 3H) |
| 78 | m-$CF_3$ | 3-F | 4-F | $CH_3$ | 8.40~6.90(m, 8H), 4.0(s, 3H) |
| 79 | m-$CF_3$ | 3-F | 5-F | $CH_3$ | 8.50~6.60(m, 8H), 3.95(s, 3H) |
| 80 | m-$CF_3OCF—HCF_2O$ | 4-$CF_3$ | H | $CH_3$ | 8.6~7.15(m, 9H), 6.5~5.4(d, t 1H), 3.95(s, 3H) |
| 81 | m-$CF_2BrO$ | 4-$CF_3$ | H | $CH_3$ | 8.6~7.2(m, 9H), 3.95(s, 3H) |
| 82 | m-$CF_2Br—CF_2O$ | 4-$CF_3$ | H | $CH_3$ | 8.65~8.40(m, 3H), 8.25~8.0(m, 2H), 7.85~7.2(m, 4H), 4.0(s, 3H) |
| 83 | m-$CF_2HCF_2O$ | 4-$CF_3$ | H | $CH_3$ | 8.7~7.2(m, 9H), 6.85(t, 0.25H), 5.95(t, 0.5H), 5.05(t, 0.25H), 3.95(s, 3H) |

*Solvent: $CDCl_3$ + DMSO-$d_6$

The compound represented by the formula (IV) is prepared by reacting a compound of the formula:

(I-5)

[wherein R' is a methoxymethoxy group at the ortho or meta position; and $R^2$, $R^3$ and $R^4$ are each as defined above] with an acid. The reaction is usually carried out with a solvent at a temperature of 20° to 100° C. for a period of 1 to 5 hours.

Normally, the acid is used in an amount of 1 to 10 equivalents to one equivalent of the compound (I-5).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chlorobenzene, dichlorobenzene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), alcohols (e.g., methanol, ethanol, isopropanol, t-butanol), water, and mixtures thereof.

The acid includes organic acids (e.g., acetic acid), inorganic acids (e.g., hydrochloric acid, sulfuric acid), and Lewis acids (e.g., fluoroborane ether complex).

After completion of the reaction, the reaction mixture is subjected to the usual after-treatment such as extraction with organic solvents, concentration, etc., and if necessary, purified by chromatography, recrystallization, etc. to obtain the desired compound.

PRODUCTION EXAMPLE 7

8 g of 2-(4-fluorophenyl)-4-(3-methoxymethoxyphenyl)-5-methoxypyrimidine was added to a mixture of 150 ml of tetrahydrofuran and 150 ml of isopropyl alcohol. After adding 10 ml of 12N hydrochloric acid thereto, the mixture was stirred for 3 hours at 60° C. The solvent was distilled away under reduced pressure. The residue was washed with water, and then dried to obtain 7 g of 2-(fluorophenyl)-4-(3-hydroxyphenyl)-5-methoxypyrimidine.

The compounds, which are used as a starting material for the compounds of the present invention, can be produced by the following procedures:

Procedure (a):

The compound (II-1) is prepared by reacting a compound of the formula (VIII-1):

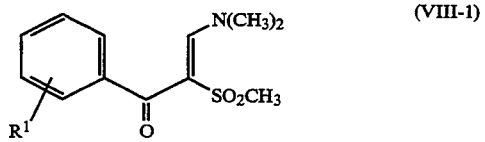

(VIII-1)

[wherein $R^1$ is as defined above] with a compound of the formula (IX-1):

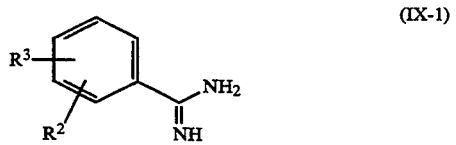

(IX-1)

[wherein $R^2$ and $R^3$ are each as defined above].

The reaction is usually carried out in a solvent at a temperature of about 20° to 100° C. for a period of about 0.5 to 5 hours.

Normally, the compound (IX-1) is used in an amount of about 1.1 to 1.2 equivalents to one equivalent of the compound (VIII-1).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chlorobenzene, dichlorobenzene), ethers (e.g., diethyl ether, diisopropyl ether, dioxane, tetrahydrofuran, diethylene glycol dimethyl ether), alcohols (e.g., methanol, ethanol, isopropanol), acid amides (e.g., N,N-dimethylformamide, acetamide), sulfur compounds (e.g., dimethyl sulfoxide, sulfolane), and mixtures thereof.

In the above reaction, the compound (IX-1) is normally used in the form of adducts of acids (e.g., a salt of hydrochloric acid). In this case, inorganic bases (e.g., potassium carbonate) or alkali metal alkoxides (e.g., sodium methoxide, sodium ethoxide) are used.

After completion of the reaction, the reaction mixture is subjected to the usual after-treatment such as extraction with organic solvents, concentration, etc., and if necessary, purified by chromatography, recrystallization, etc.

Further, the benzamidine derivative represented by the formula (IX-1) is either a well known compound or produced by an ordinary method.

Procedure (b):

The compound represented by the formula (VIII-1) is prepared by reacting a compound of the formula (X):

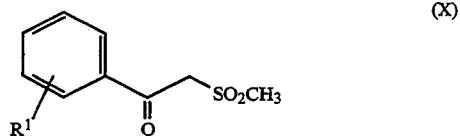

(X)

[wherein $R^1$ is as defined above] with N,N-dimethylformamide dimethylacetal. The reaction is usually carried out with or without a solvent at a temperature of 20° to 150° C. for a period of about 0.5 to 10 hours.

Normally, N,N-dimethylformamide dimethylacetal is used in an amount of 1.0 to 1.5 equivalents to one equivalent of the compound (X).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chloroform, carbon tetrachloride, dichloroethane, chlorobenzene, dichlorobenzene), ethers (e.g., diethyl ether, diisopropyl ether, dioxane, tetrahydrofuran, diethylene glycol dimethyl ether), alcohols (e.g., methanol, ethanol, isopropanol, t-butanol, octanol, cyclohexanol, methylcellosolve, diethylene glycol, glycerin), acid amides (e.g., N,N-dimethylformamide), sulfur compounds (e.g., dimethyl sulfoxide, sulfolane), and mixtures thereof.

The derivative represented by the formula (X) may be produced by a method described, for example, in J. Org. Chem., 29, 2329 (1964); J. Am. Chem. Soc., 77, 5063 (1955); J. Org. Chem., 28, 1896 (1963). The derivative represented by the formula (X) is produced in the presence of sodium hydroxide.

Procedure (c):

The compound (II-1)' is prepared by reacting a compound of the formula (II-2):

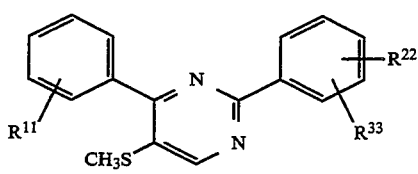

(II-2)

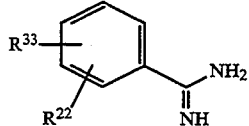

(IX-2)

[wherein $R^{11}$ represents a hydrogen atom, or a halogen atom, a ($C_1$ to $C_3$)-alkyl group, a halo-($C_1$ to $C_3$)-alkyl group, a ($C_1$ to $C_6$)-alkoxy group, a ($C_2$ to $C_6$)-alkynyloxy group, a ($C_2$ to $C_6$)-alkenyloxy group, a halo-($C_2$ to $C_6$)-alkynyloxy group, a halo-($C_2$ to $C_6$)-alkenyloxy group, a halo-($C_1$ to $C_6$)-alkoxy group, a phenoxy group or a ($C_1$ to $C_2$)-alkoxy-($C_1$ to $C_2$)-alkoxy group, at the ortho or meta position; $R^{22}$ and $R^{33}$, which may be either the same or different, each represents a hydrogen atom, a halogen atom, a ($C_1$ to $C_2$)-alkyl group, a halo-($C_1$ to $C_2$)-alkyl group, a ($C_1$ to $C_2$)-alkoxy group, or a halo-($C_1$ to $C_2$)-alkoxy group; provided that $R^{11}$, $R^{22}$ and $R^{33}$ are not a hydrogen atom at the same time and that both of $R^{22}$ and $R^{33}$, if each representing a substituent other than a hydrogen atom, are not at the ortho position for the pyrimidine ring at the same time with a compound of the formula:

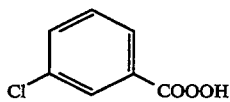

The reaction is usually carried out in a solvent at a temperature of about 0° to 40° C. for a period of about 0.5 to 10 hours. The meta-chloroperbenzoic acid is used in an amount of 2 to 3 mol per mol of the pyrimidine derivative represented by the formula (II-2).

The solvent includes halogenated hydrocarbons (e.g., chloroform, carbon tetrachloride, dichloroethane, chlorobenzene, dichlorobenzene).

After completion of the reaction, the reaction mixture is subjected to the usual after-treatment such as extraction with organic solvents, concentration, etc., and if necessary, purified by chromatography, recrystallization, etc. to obtain the target compound of the invention.

Procedure (d):

The compound (II-2) is prepared by reacting a compound of the formula (VIII-2):

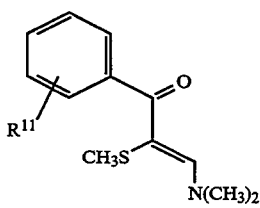

(VIII-2)

[wherein $R^{11}$ is as defined above] with a compound of the formula (IX-2):

[wherein $R^{22}$ and $R^{33}$ are each as defined above].

The reaction is usually carried out in a solvent at a temperature of about 20° to 100° C. for a period of about 2 to 10 hours.

Normally, the compound (IX-2) is used in an amount of about 1.1 to 2.0 equivalents to one equivalent of the compound (VIII-2).

The solvent includes aliphatic hydrocarbons (e.g., hexane, heptane, ligroin, petroleum ether), aromatic hydrocarbons (e.g., benzene, toluene, xylene), halogenated hydrocarbons (e.g., chlorobenzene, dichlorobenzene), ethers (e.g., diethyl ether, diisopropyl ether, dioxane, tetrahydrofuran, diethylene glycol dimethyl ether), alcohols (e.g., methanol, ethanol, isopropanol), acid amides (e.g., N,N-dimethylformamide, acetamide), sulfur compounds (e.g., dimethyl sulfoxide, sulfolane), and mixtures thereof.

In the above reaction, the compound (IX-2) is normally used in the form of adducts of acids (e.g., a salt of hydrochloric acid). In this case, inorganic bases (e.g., potassium carbonate) or alkali metal alkoxides (e.g., sodium methoxide, sodium ethoxide) are used.

After completion of the reaction, the reaction mixture is subjected to the usual after-treatment such as extraction with organic solvents, concentration, etc., and if necessary, purified by chromatography, recrystallization, etc.

Further, the benzamidine derivative represented by the formula (IX-2) is either a well known compound or produced by an ordinary method.

Procedure (e):

The compound (VIII-2) is prepared by reacting a compound of the formula (VIII-3):

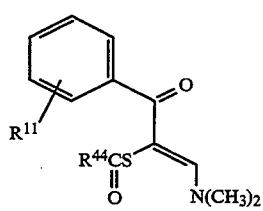

(VIII-3)

[wherein $R^{11}$ is as defined above and $R^{44}$ is a ($C_1$ to $C_3$)-alkoxy group] with a compound of the formula:

CH$_3$I

The reaction is usually carried out in a solvent in the presence of a base at a temperature of 0° to 50° C. for 0.5 to 10 hours. Methyl iodide is used in an amount of about 1.5 mol while the base is used in an amount of about 1.0 to 1.2 mol each per mol of the ethane derivative of the formula (VIII-3).

The solvent includes alcohols (e.g., methanol, ethanol, isopropanol). Examples of the base include sodium hydroxide, potassium hydroxide, sodium carbonate and potassium carbonate.

After completion of the reaction, the reaction mixture is neutralized with an acid and subjected to the usual after-treatment such as extraction with organic solvents, concentration, etc., and if necessary, purified by chromatography, distillation, etc. Thus the target compound of the present invention can be obtained.

Procedure (f):

The compound (VIII-3) is prepared by reacting a compound of the formula (XI):

[wherein $R^{11}$ is as defined above] with a compound of the formula (XII):

[wherein $R^{44}$ is as defined above and X is a bromine atom or a chlorine atom].

The reaction is usually carried out either without using any solvent or in a solvent in the presence of a base at a temperature of 0° to 40° C. for 0.1 to 5 hours. The alkoxycarbonylsulfenyl halide of the formula (XII) is used in an amount of 1.0 to 1.5 mol while the base is used in an amount of 1.2 to 2.0 mol each per mol of the ethene derivative of the formula (XI).

The solvent includes aliphatic hydrocarbons (e.g., hexane, heptane) and aromatic hydrocarbons (e.g., benzene, toluene, xylene). Examples of the base include pyridine, triethylamine, etc.

After completion of the reaction, the reaction mixture is treated with an aqueous solution of sodium hydrogencarbonate and subjected to the usual after-treatment such as extraction with organic solvents, concentration, etc., and if necessary, purified by chromatography, distillation, etc. Thus the target compound of the present invention can be obtained.

The 1-(N,N-dimethylamino)-2-benzoylethene derivative represented by the formula (XI) and the alkoxycarbonylsulfenyl halide represented by the formula (XII) may be respectively produced by methods described, for example, in Chem. Ber., 97, 3397 (1964) and Angew. Chem. Internat. Edit., 9, 54 (1970).

Examples of Compound (II) {(II-1), (II-1)' and (II-2)} which can be produced by the procedures (a), (c) and (d) include those shown in Table 3. However, it is a matter of course that the present invention is not restricted thereby.

TABLE 3

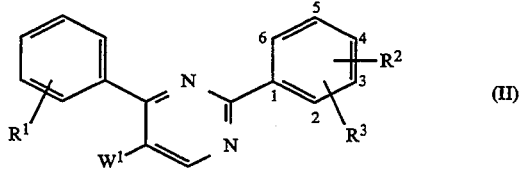

| $R^1$ | $R^2$ | $R^3$ | $W^1$ |
|---|---|---|---|
| H | 4-Cl | H | $CH_3SO_2$ |
| H | 4-Br | H | $CH_3SO_2$ |
| H | 4-$CF_3$ | H | $CH_3SO_2$ |
| H | 4-$NO_2$ | H | $CH_3SO_2$ |
| m-F | H | H | $CH_3SO_2$ |
| m-F | 4-$CH_3$ | H | $CH_3SO_2$ |
| m-F | 4-F | H | $CH_3SO_2$ |
| m-F | 4-$CF_3$ | H | $CH_3SO_2$ |
| m-F | 4-Cl | H | $CH_3SO_2$ |
| m-F | 4-Br | H | $CH_3SO_2$ |
| m-Cl | 4-F | H | $CH_3SO_2$ |
| m-Cl | H | H | $CH_3SO_2$ |
| m-Cl | 4-Cl | H | $CH_3SO_2$ |
| m-Cl | 4-$CF_3$ | H | $CH_3SO_2$ |
| m-Br | H | H | $CH_3SO_2$ |
| m-Br | 4-Cl | H | $CH_3SO_2$ |
| m-Br | 4-Br | H | $CH_3SO_2$ |
| m-Br | 4-$CF_3$ | H | $CH_3SO_2$ |
| m-Br | 4-$NO_2$ | H | $CH_3SO_2$ |
| o-Br | 4-$CF_3$ | H | $CH_3SO_2$ |
| m-I | 4-$CF_3$ | H | $CH_3SO_2$ |
| m-I | 4-F | H | $CH_3SO_2$ |
| m-$CH_3$ | 4-F | H | $CH_3SO_2$ |
| m-$CH_3$ | 4-$CF_3$ | H | $CH_3SO_2$ |
| o-$CH_3$ | 4-$CF_3$ | H | $CH_3SO_2$ |
| m-$CF_3$ | H | H | $CH_3SO_2$ |
| m-$CF_3$ | 4-$CH_3$ | H | $CH_3SO_2$ |
| m-$CF_3$ | 4-F | H | $CH_3SO_2$ |
| m-$CF_3$ | 4-Cl | H | $CH_3SO_2$ |
| m-$CF_3$ | 4-Br | H | $CH_3SO_2$ |
| m-$CF_3$ | 4-$CF_3$ | H | $CH_3SO_2$ |
| m-$CF_3$ | 4-$CH_3O$ | H | $CH_3SO_2$ |
| m-$CF_3$ | 3-$CH_3O$ | H | $CH_3SO_2$ |
| m-$CF_3$ | 3-F | H | $CH_3SO_2$ |
| m-$CF_3$ | 2-F | H | $CH_3SO_2$ |
| o-$CF_3$ | 4-$CF_3$ | H | $CH_3SO_2$ |
| o-$CF_3$ | 2-F | H | $CH_3SO_2$ |
| m-$CH_3O$ | 4-F | H | $CH_3SO_2$ |
| m-$CH_3O$ | 4-$CF_3$ | H | $CH_3SO_2$ |
| m-$C_2H_5O$ | 4-F | H | $CH_3SO_2$ |
| m-$C_2H_5O$ | 4-$CF_3$ | H | $CH_3SO_2$ |
| m-(i)$C_3H_7O$ | 4-F | H | $CH_3SO_2$ |
| m-(sec)$C_4H_9O$ | 4-F | H | $CH_3SO_2$ |
| m-(sec)$C_4H_9O$ | 4-$CF_3$ | H | $CH_3SO_2$ |
| m-$CH_2$=$CHCH_2O$ | 4-F | H | $CH_3SO_2$ |
| m-$CH_2$=$CHCH_2O$ | 4-$CF_3$ | H | $CH_3SO_2$ |
| m-CH≡$CCH_2O$ | 4-F | H | $CH_3SO_2$ |
| m-CH≡$CCH_2O$ | 4-$CF_3$ | H | $CH_3SO_2$ |
| m-$CH_3S$ | 4-F | H | $CH_3SO_2$ |
| m-$CH_3S$ | 4-$CF_3$ | H | $CH_3SO_2$ |
| m-$CF_3O$ | 4-$CF_3$ | H | $CH_3SO_2$ |
| m-$CF_3O$ | 4-F | H | $CH_3SO_2$ |
| m-$CF_3O$ | 4-Cl | H | $CH_3SO_2$ |
| m-$CCl_3O$ | 4-F | H | $CH_3SO_2$ |
| m-$CCl_3O$ | 4-$CF_3$ | H | $CH_3SO_2$ |
| m-$CF_2HO$ | 4-F | H | $CH_3SO_2$ |
| m-$CF_2HO$ | 4-$CF_3$ | H | $CH_3SO_2$ |
| m-$CF_2ClO$ | 4-F | H | $CH_3SO_2$ |
| m-$CF_2ClO$ | 4-$CF_3$ | H | $CH_3SO_2$ |
| m-$CF_3CF_2O$ | 4-F | H | $CH_3SO_2$ |
| m-$CF_3CF_2O$ | 4-$CF_3$ | H | $CH_3SO_2$ |
| m-$CF_2HCF_2O$ | 4-F | H | $CH_3SO_2$ |
| m-$CF_2HCF_2O$ | 4-$CF_3$ | H | $CH_3SO_2$ |
| m-$CCl_2HCF_2O$ | 4-F | H | $CH_3SO_2$ |
| m-$CCl_2HCF_2O$ | 4-$CF_3$ | H | $CH_3SO_2$ |
| m-$CF_3S$ | 4-F | H | $CH_3SO_2$ |
| m-$CF_3S$ | 4-$CF_3$ | H | $CH_3SO_2$ |
| m-$C_6H_5O$ | 4-F | H | $CH_3SO_2$ |
| m-$C_6H_5O$ | 4-$CF_3$ | H | $CH_3SO_2$ |
| m-$CH_3CO_2$ | 4-F | H | $CH_3SO_2$ |
| m-$CH_3CO_2$ | 4-$CF_3$ | H | $CH_3SO_2$ |

TABLE 3-continued

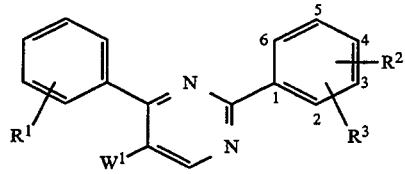

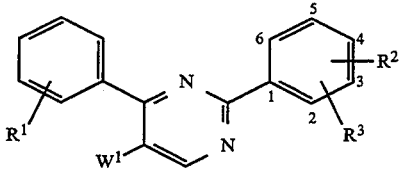

(II)

| R¹ | R² | R³ | W¹ |
|---|---|---|---|
| m-CClFHCF₂O | 4-F | H | CH₃SO₂ |
| m-CClFHCF₂O | 4-CF₃ | H | CH₃SO₂ |
| m-CClFHCClFO | 4-F | H | CH₃SO₂ |
| m-CClFHCClFO | 4-CF₃ | H | CH₃SO₂ |
| m-CF₃CO₂ | 4-F | H | CH₃SO₂ |
| m-CH₃OCH₂O | 4-F | H | CH₃SO₂ |
| m-CH₃OCH₂O | 4-CF₃ | H | CH₃SO₂ |
| m-CH₃SO₃ | 4-F | H | CH₃SO₂ |
| m-CH₃SO₃ | 4-CF₃ | H | CH₃SO₂ |
| m-CH₃CH₂SO₃ | 4-F | H | CH₃SO₂ |
| m-CH₃CH₂SO₃ | 4-CF₃ | H | CH₃SO₂ |
| m-CF₃SO₃ | 4-F | H | CH₃SO₂ |
| m-CF₃SO₃ | 4-CF₃ | H | CH₃SO₂ |
| m-CF₃CF₂SO₃ | 4-F | H | CH₃SO₂ |
| m-CF₃CF₂SO₃ | 4-CF₃ | H | CH₃SO₂ |
| m-CF₃O | 4-CF₃O | H | CH₃SO₂ |
| m-CF₃ | 4-CF₃O | H | CH₃SO₂ |
| m-CH₂NH₂ | 4-CF₃ | H | CH₃SO₂ |
| m-CH₂NH₂ | 4-F | H | CH₃SO₂ |
| m-CF₃O | 4-SCH₃ | H | CH₃SO₂ |
| m-CF₃ | 4-SCH₃ | H | CH₃SO₂ |
| m-CN | 4-CF₃ | H | CH₃SO₂ |
| m-CN | 4-F | H | CH₃SO₂ |
| m-COOCH₃ | 4-CF₃ | H | CH₃SO₂ |
| m-COOCH₃ | 4-F | H | CH₃SO₂ |
| m-CClF=CFO | 4-F | H | CH₃SO₂ |
| m-CF₃O | 4-SCF₃ | H | CH₃SO₂ |
| m-CF₃ | 4-SCF₃ | H | CH₃SO₂ |
| H | 4-F | H | CH₃SO₂ |
| H | 3-F | H | CH₃SO₂ |
| H | 3-CF₃ | H | CH₃SO₂ |
| H | 4-CH₃ | H | CH₃SO₂ |
| m-F | 3-F | H | CH₃SO₂ |
| m-F | 3-CF₃ | H | CH₃SO₂ |
| m-Cl | 3-F | H | CH₃SO₂ |
| m-Cl | 3-CF₃ | H | CH₃SO₂ |
| m-Cl | 4-CH₃ | H | CH₃SO₂ |
| m-CF₃ | 3-CF₃ | H | CH₃SO₂ |
| m-(i)C₃H₇O | H | H | CH₃SO₂ |
| m-(i)C₃H₇O | 4-CF₃ | H | CH₃SO₂ |
| m-(i)C₃H₇O | 3-F | H | CH₃SO₂ |
| m-(i)C₃H₇O | 3-CF₃ | H | CH₃SO₂ |
| m-(i)C₃H₇O | 4-Cl | H | CH₃SO₂ |
| m-(i)C₃H₇O | 4-CH₃ | H | CH₃SO₂ |
| m-(sec)C₄H₉O | H | H | CH₃SO₂ |
| m-(sec)C₄H₉O | 3-F | H | CH₃SO₂ |
| m-(sec)C₄H₉O | 3-CF₃ | H | CH₃SO₂ |
| m-(sec)C₄H₉O | 4-Cl | H | CH₃SO₂ |
| m-(sec)C₄H₉O | 4-CH₃ | H | CH₃SO₂ |
| m-CF₃O | H | H | CH₃SO₂ |
| m-CF₃O | 3-F | H | CH₃SO₂ |
| m-CF₃O | 3-CF₃ | H | CH₃SO₂ |
| m-CF₃O | 4-CH₃ | H | CH₃SO₂ |
| O-CF₃ | H | H | CH₃SO₂ |
| O-CF₃ | 4-F | H | CH₃SO₂ |
| O-CF₃ | 3-F | H | CH₃SO₂ |
| O-CF₃ | 3-CF₃ | H | CH₃SO₂ |
| O-CF₃ | 4-Cl | H | CH₃SO₂ |
| O-CF₃ | 4-CH₃ | H | CH₃SO₂ |
| H | 2-F | 4-Cl | CH₃SO₂ |
| H | 3-F | 4-Cl | CH₃SO₂ |
| H | 2-F | 4-Br | CH₃SO₂ |
| H | 3-F | 4-F | CH₃SO₂ |
| H | 2-F | 4-CF₃ | CH₃SO₂ |
| H | 3-F | 4-CF₃ | CH₃SO₂ |
| m-F | 2-F | 4-F | CH₃SO₂ |
| m-F | 3-F | 4-F | CH₃SO₂ |
| m-F | 2-F | 4-CF₃ | CH₃SO₂ |
| m-F | 3-F | 4-CF₃ | CH₃SO₂ |
| m-F | 2-F | 4-Cl | CH₃SO₂ |
| m-F | 3-F | 4-Cl | CH₃SO₂ |
| m-F | 2-F | 4-Br | CH₃SO₂ |
| m-F | 3-F | 4-Br | CH₃SO₂ |
| m-Cl | 2-F | 4-F | CH₃SO₂ |
| m-Cl | 3-F | 4-F | CH₃SO₂ |
| m-Cl | 2-F | 4-Cl | CH₃SO₂ |
| m-Cl | 3-F | 4-Cl | CH₃SO₂ |
| m-Cl | 2-F | 4-CF₃ | CH₃SO₂ |
| m-Cl | 3-F | 4-CF₃ | CH₃SO₂ |
| o-Br | 2-F | 4-CF₃ | CH₃SO₂ |
| o-Br | 3-F | 4-CF₃ | CH₃SO₂ |
| m-I | 2-F | 4-CF₃ | CH₃SO₂ |
| m-I | 3-F | 4-CF₃ | CH₃SO₂ |
| m-I | 2-F | 4-F | CH₃SO₂ |
| m-I | 3-F | 4-F | CH₃SO₂ |
| m-CH₃ | 2-F | 4-F | CH₃SO₂ |
| m-CH₃ | 3-F | 4-F | CH₃SO₂ |
| m-CH₃ | 2-F | 4-CF₃ | CH₃SO₂ |
| m-CH₃ | 3-F | 4-CF₃ | CH₃SO₂ |
| o-CH₃ | 2-F | 4-CF₃ | CH₃SO₂ |
| o-CH₃ | 3-F | 4-CF₃ | CH₃SO₂ |
| m-CF₃ | 3-F | 5-F | CH₃SO₂ |
| m-CF₃ | 2-F | 4-F | CH₃SO₂ |
| m-CF₃ | 3-F | 4-F | CH₃SO₂ |
| m-CF₃ | 2-F | 4-Cl | CH₃SO₂ |
| m-CF₃ | 3-F | 4-Cl | CH₃SO₂ |
| m-CF₃ | 2-F | 4-CF₃ | CH₃SO₂ |
| m-CF₃ | 3-F | 4-CF₃ | CH₃SO₂ |
| m-CF₃ | 3-CF₃ | 4-F | CH₃SO₂ |
| m-CF₃ | 3-Cl | 4-F | CH₃SO₂ |
| m-CH₃O | 2-F | 4-F | CH₃SO₂ |
| m-CH₃O | 3-F | 4-F | CH₃SO₂ |
| m-CH₃O | 2-F | 4-CF₃ | CH₃SO₂ |
| m-CH₃O | 3-F | 4-CF₃ | CH₃SO₂ |
| m-C₂H₅O | 2-F | 4-F | CH₃SO₂ |
| m-C₂H₅O | 3-F | 4-F | CH₃SO₂ |
| m-C₂H₅O | 2-F | 4-CF₃ | CH₃SO₂ |
| m-C₂H₅O | 3-F | 4-CF₃ | CH₃SO₂ |
| m-(i)C₃H₇O | 2-F | 4-F | CH₃SO₂ |
| m-(i)C₃H₇O | 3-F | 4-F | CH₃SO₂ |
| m-(sec)C₄H₉O | 2-F | 4-F | CH₃SO₂ |
| m-(sec)C₄H₉O | 3-F | 4-F | CH₃SO₂ |
| m-(sec)C₄H₉O | 2-F | 4-CF₃ | CH₃SO₂ |
| m-(sec)C₄H₉O | 3-F | 4-CF₃ | CH₃SO₂ |
| m-CH₂=CHCH₂O | 2-F | 4-F | CH₃SO₂ |
| m-CH₂=CHCH₂O | 3-F | 4-F | CH₃SO₂ |
| m-CH₂=CHCH₂O | 2-F | 4-CF₃ | CH₃SO₂ |
| m-CH₂=CHCH₂O | 3-F | 4-CF₃ | CH₃SO₂ |
| m-CH≡CCH₂O | 2-F | 4-F | CH₃SO₂ |
| m-CH≡CCH₂O | 3-F | 4-F | CH₃SO₂ |
| m-CH≡CCH₂O | 2-F | 4-CF₃ | CH₃SO₂ |
| m-CH≡CCH₂O | 3-F | 4-CF₃ | CH₃SO₂ |
| m-CH₃S | 2-F | 4-F | CH₃SO₂ |
| m-CH₃S | 3-F | 4-F | CH₃SO₂ |
| m-CH₃S | 2-F | 4-CF₃ | CH₃SO₂ |
| m-CH₃S | 3-F | 4-CF₃ | CH₃SO₂ |
| m-CF₃O | 2-F | 4-CF₃ | CH₃SO₂ |
| m-CF₃O | 3-F | 4-CF₃ | CH₃SO₂ |
| m-CF₃O | 3-CF₃ | 4-F | CH₃SO₂ |
| m-CF₃O | 2-F | 4-F | CH₃SO₂ |
| m-CF₃O | 3-F | 4-F | CH₃SO₂ |
| m-CF₃O | 2-F | 4-Cl | CH₃SO₂ |
| m-CF₃O | 3-F | 4-Cl | CH₃SO₂ |
| m-CF₃O | 3-Cl | 4-F | CH₃SO₂ |
| m-CCl₃O | 2-F | 4-F | CH₃SO₂ |
| m-CCl₃O | 3-F | 4-F | CH₃SO₂ |
| m-CCl₃O | 2-F | 4-CF₃ | CH₃SO₂ |
| m-CCl₃O | 3-F | 4-CF₃ | CH₃SO₂ |
| m-CF₂HO | 2-F | 4-F | CH₃SO₂ |
| m-CF₂HO | 3-F | 4-F | CH₃SO₂ |
| m-CF₂HO | 2-F | 4-CF₃ | CH₃SO₂ |
| m-CF₂HO | 3-F | 4-CF₃ | CH₃SO₂ |

TABLE 3-continued

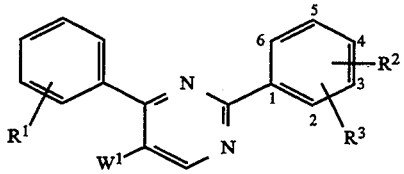

(II)

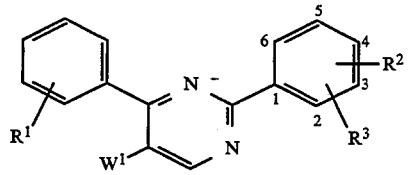

(II)

| R¹ | R² | R³ | W¹ | R¹ | R² | R³ | W¹ |
| --- | --- | --- | --- | --- | --- | --- | --- |
| m-CF₂ClO | 2-F | 4-F | CH₃SO₂ | m-COOCH₃ | 3-F | 4-F | CH₃SO₂ |
| m-CF₂ClO | 3-F | 4-F | CH₃SO₂ | m-COOCH₃ | 2-F | 4-CF₃ | CH₃SO₂ |
| m-CF₂ClO | 2-F | 4-CF₃ | CH₃SO₂ | m-COOCH₃ | 3-F | 4-CF₃ | CH₃SO₂ |
| m-CF₂ClO | 3-F | 4-CF₃ | CH₃SO₂ | m-CF₂BrO | 4-F | H | CH₃SO₂ |
| m-CF₃CF₂O | 2-F | 4-F | CH₃SO₂ | m-CF₂BrO | 4-CF₃ | H | CH₃SO₂ |
| m-CF₃CF₂O | 3-F | 4-F | CH₃SO₂ | m-CF₂BrCF₂O | 4-F | H | CH₃SO₂ |
| m-CF₃CF₂O | 2-F | 4-CF₃ | CH₃SO₂ | m-CF₂BrCF₂O | 4-CF₃ | H | CH₃SO₂ |
| m-CF₃CF₂O | 3-F | 4-CF₃ | CH₃SO₂ | m-CF₃OCFHCF₂O | 4-F | H | CH₃SO₂ |
| m-CF₂HCF₂O | 2-F | 4-F | CH₃SO₂ | m-CF₃OCFHCF₂O | 4-CF₃ | H | CH₃SO₂ |
| m-CF₂HCF₂O | 3-F | 4-F | CH₃SO₂ | m-Br | H | H | CH₃S |
| m-CF₂HCF₂O | 2-F | 4-CF₃ | CH₃SO₂ | m-Br | 4-CF₃ | H | CH₃S |
| m-CF₂HCF₂O | 3-F | 4-CF₃ | CH₃SO₂ | m-Br | 4-Cl | H | CH₃S |
| m-CCl₂HCF₂O | 2-F | 4-F | CH₃SO₂ | m-Br | 4-Br | H | CH₃S |
| m-CCl₂HCF₂O | 3-F | 4-F | CH₃SO₂ | o-Br | 4-CF₃ | H | CH₃S |
| m-CCl₂HCF₂O | 2-F | 4-CF₃ | CH₃SO₂ | m-CH₃ | 4-F | H | CH₃S |
| m-CCl₂HCF₂O | 3-F | 4-CF₃ | CH₃SO₂ | m-CH₃ | 4-CF₃ | H | CH₃S |
| m-CF₂BrO | 2-F | 4-F | CH₃SO₂ | o-CH₃ | 4-CF₃ | H | CH₃S |
| m-CF₂BrO | 3-F | 4-F | CH₃SO₂ | m-CF₃ | 4-CH₃O | H | CH₃S |
| m-CF₂BrO | 2-F | 4-CF₃ | CH₃SO₂ | m-CF₃ | 3-CH₃O | H | CH₃S |
| m-CF₂BrO | 3-F | 4-CF₃ | CH₃SO₂ | o-CF₃ | 2-F | H | CH₃S |
| m-CF₃S | 2-F | 4-F | CH₃SO₂ | m-CF₂ClO | 4-F | H | CH₃S |
| m-CF₃S | 3-F | 4-F | CH₃SO₂ | m-CF₂ClO | 4-CF₃ | H | CH₃S |
| m-CF₃S | 2-F | 4-CF₃ | CH₃SO₂ | m-CF₃CF₂O | 4-F | H | CH₃S |
| m-CF₃S | 3-F | 4-CF₃ | CH₃SO₂ | m-CF₃CF₂O | 4-CF₃ | H | CH₃S |
| m-C₆H₅O | 2-F | 4-F | CH₃SO₂ | m-C₆H₅O | 4-F | H | CH₃S |
| m-C₆H₅O | 3-F | 4-F | CH₃SO₂ | m-C₆H₅O | 4-CF₃ | H | CH₃S |
| m-C₆H₅O | 2-F | 4-CF₃ | CH₃SO₂ | m-CH₃OCH₂O | 4-F | H | CH₃S |
| m-C₆H₅O | 3-F | 4-CF₃ | CH₃SO₂ | m-CH₃OCH₂O | 4-CF₃ | H | CH₃S |
| m-CH₃CO₂ | 2-F | 4-F | CH₃SO₂ | m-CF₃O | 4-CF₃O | H | CH₃S |
| m-CH₃CO₂ | 3-F | 4-F | CH₃SO₂ | m-CH₃ | 2-F | 4-F | CH₃S |
| m-CH₃CO₂ | 2-F | 4-CF₃ | CH₃SO₂ | o-Br | 2-F | 4-CF₃ | CH₃S |
| m-CH₃CO₂ | 3-F | 4-CF₃ | CH₃SO₂ | o-Br | 3-F | 4-CF₃ | CH₃S |
| m-CClFHCF₂O | 2-F | 4-F | CH₃SO₂ | m-CF₃ | 4-CF₃O | H | CH₃S |
| m-CClFHCF₂O | 3-F | 4-F | CH₃SO₂ | m-CH₃ | 3-F | 4-F | CH₃S |
| m-CClFHCF₂O | 2-F | 4-CF₃ | CH₃SO₂ | m-CH₃ | 2-F | 4-CF₃ | CH₃S |
| m-CClFHCF₂O | 3-F | 4-CF₃ | CH₃SO₂ | m-CH₃ | 3-F | 4-CF₃ | CH₃S |
| m-CClFHCClFO | 2-F | 4-F | CH₃SO₂ | o-CH₃ | 2-F | 4-CF₃ | CH₃S |
| m-CClFHCClFO | 3-F | 4-F | CH₃SO₂ | o-CH₃ | 3-F | 4-CF₃ | CH₃S |
| m-CClFHCClFO | 2-F | 4-CF₃ | CH₃SO₂ | m-CF₃ | 2-F | 4-Cl | CH₃S |
| m-CClFHCClFO | 3-F | 4-CF₃ | CH₃SO₂ | m-CF₃ | 3-F | 4-Cl | CH₃S |
| m-CF₃CO₂ | 2-F | 4-F | CH₃SO₂ | m-CF₃ | 3-F | 4-CF₃ | CH₃S |
| m-CF₃CO₂ | 3-F | 4-F | CH₃SO₂ | m-CF₃ | 3-CF₃ | 4-F | CH₃S |
| m-CH₃OCH₂O | 2-F | 4-F | CH₃SO₂ | m-CF₃ | 3-Cl | 4-F | CH₃S |
| m-CH₃OCH₂O | 3-F | 4-F | CH₃SO₂ | m-CH₃O | 2-F | 4-F | CH₃S |
| m-CH₃OCH₂O | 2-F | 4-CF₃ | CH₃SO₂ | m-CH₃O | 3-F | 4-F | CH₃S |
| m-CH₃OCH₂O | 3-F | 4-CF₃ | CH₃SO₂ | m-CH₃O | 2-F | 4-CF₃ | CH₃S |
| m-CH₃SO₃ | 2-F | 4-F | CH₃SO₂ | m-CH₃O | 3-F | 4-CF₃ | CH₃S |
| m-CH₃SO₃ | 3-F | 4-F | CH₃SO₂ | m-C₂H₅O | 2-F | 4-F | CH₃S |
| m-CH₃SO₃ | 2-F | 4-CF₃ | CH₃SO₂ | m-C₂H₅O | 2-F | 4-CF₃ | CH₃S |
| m-CH₃SO₃ | 3-F | 4-CF₃ | CH₃SO₂ | m-C₂H₅O | 3-F | 4-CF₃ | CH₃S |
| m-C₂H₅SO₃ | 2-F | 4-F | CH₃SO₂ | m-(i)C₃H₇O | 2-F | 4-F | CH₃S |
| m-C₂H₅SO₃ | 3-F | 4-F | CH₃SO₂ | m-(sec)C₄H₉O | 2-F | 4-F | CH₃S |
| m-C₂H₅SO₃ | 2-F | 4-CF₃ | CH₃SO₂ | m-(sec)C₄H₉O | 2-F | 4-CF₃ | CH₃S |
| m-C₂H₅SO₃ | 3-F | 4-CF₃ | CH₃SO₂ | m-(sec)C₄H₉O | 3-F | 4-CF₃ | CH₃S |
| m-CF₃SO₃ | 2-F | 4-F | CH₃SO₂ | m-CF₃O | 2-F | 4-CF₃ | CH₃S |
| m-CF₃SO₃ | 3-F | 4-F | CH₃SO₂ | m-CF₃O | 3-F | 4-CF₃ | CH₃S |
| m-CF₃SO₃ | 2-F | 4-CF₃ | CH₃SO₂ | m-CF₃O | 3-CF₃ | 4-F | CH₃S |
| m-CF₃SO₃ | 3-F | 4-CF₃ | CH₃SO₂ | m-CF₃O | 2-F | 4-Cl | CH₃S |
| m-CF₃CF₂SO₃ | 2-F | 4-F | CH₃SO₂ | m-CF₃O | 3-F | 4-Cl | CH₃S |
| m-CF₃CF₂SO₃ | 3-F | 4-F | CH₃SO₂ | m-CF₂ClO | 2-F | 4-F | CH₃S |
| m-CF₃CF₂SO₃ | 2-F | 4-CF₃ | CH₃SO₂ | m-CF₂ClO | 3-F | 4-F | CH₃S |
| m-CF₃CF₂SO₃ | 3-F | 4-CF₃ | CH₃SO₂ | m-CF₂ClO | 2-F | 4-CF₃ | CH₃S |
| m-CH₂NH₂ | 2-F | 4-F | CH₃SO₂ | m-CF₂ClO | 3-F | 4-CF₃ | CH₃S |
| m-CH₂NH₂ | 3-F | 4-F | CH₃SO₂ | m-CF₃CF₂O | 2-F | 4-F | CH₃S |
| m-CH₂NH₂ | 2-F | 4-CF₃ | CH₃SO₂ | m-CF₃CF₂O | 3-F | 4-F | CH₃S |
| m-CH₂NH₂ | 3-F | 4-CF₃ | CH₃SO₂ | m-CF₃CF₂O | 2-F | 4-CF₃ | CH₃S |
| m-CN | 2-F | 4-F | CH₃SO₂ | m-CF₃CF₂O | 3-F | 4-CF₃ | CH₃S |
| m-CN | 3-F | 4-F | CH₃SO₂ | m-CF₂BrO | 2-F | 4-F | CH₃S |
| m-CN | 2-F | 4-CF₃ | CH₃SO₂ | m-CF₂BrO | 3-F | 4-F | CH₃S |
| m-CN | 3-F | 4-CF₃ | CH₃SO₂ | m-CF₂BrO | 2-F | 4-CF₃ | CH₃S |
| m-COOCH₃ | 2-F | 4-F | CH₃SO₂ | m-CF₂BrO | 3-F | 4-CF₃ | CH₃S |
| | | | | m-C₆H₅O | 2-F | 4-F | CH₃S |

TABLE 3-continued

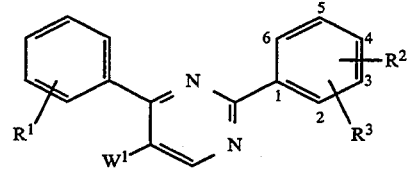
(II)

| R¹ | R² | R³ | W¹ |
|---|---|---|---|
| m-C$_6$H$_5$O | 3-F | 4-F | CH$_3$S |
| m-C$_6$H$_5$O | 2-F | 4-CF$_3$ | CH$_3$S |
| m-C$_6$H$_5$O | 3-F | 4-CF$_3$ | CH$_3$S |
| m-CH$_3$OCH$_2$O | 2-F | 4-F | CH$_3$S |
| m-CH$_3$OCH$_2$O | 3-F | 4-F | CH$_3$S |
| m-CH$_3$OCH$_2$O | 2-F | 4-CF$_3$ | CH$_3$S |
| m-CH$_3$OCH$_2$O | 3-F | 4-CF$_3$ | CH$_3$S |
| H | 4-F | 3-F | CH$_3$S |
| H | 4-F | H | CH$_3$S |
| H | 4-CF$_3$ | H | CH$_3$S |
| H | 3-F | H | CH$_3$S |
| H | 3-CF$_3$ | H | CH$_3$S |
| H | 4-Cl | H | CH$_3$S |
| H | 4-CH$_3$ | H | CH$_3$S |
| m-F | H | H | CH$_3$S |
| m-F | 4-F | H | CH$_3$S |
| m-F | 4-CF$_3$ | H | CH$_3$S |
| m-F | 3-F | H | CH$_3$S |
| m-F | 3-CF$_3$ | H | CH$_3$S |
| m-F | 4-Cl | H | CH$_3$S |
| m-F | 4-CH$_3$ | H | CH$_3$S |
| m-Cl | H | H | CH$_3$S |
| m-Cl | 4-F | H | CH$_3$S |
| m-Cl | 4-CF$_3$ | H | CH$_3$S |
| m-Cl | 3-F | H | CH$_3$S |
| m-Cl | 3-CF$_3$ | H | CH$_3$S |
| m-Cl | 4-Cl | H | CH$_3$S |
| m-Cl | 4-CH$_3$ | H | CH$_3$S |
| m-CF$_3$ | H | H | CH$_3$S |
| m-CF$_3$ | 4-F | H | CH$_3$S |
| m-CF$_3$ | 4-CF$_3$ | H | CH$_3$S |
| m-CF$_3$ | 3-F | H | CH$_3$S |
| m-CF$_3$ | 3-CF$_3$ | H | CH$_3$S |
| m-CF$_3$ | 4-Cl | H | CH$_3$S |
| m-CF$_3$ | 4-CH$_3$ | H | CH$_3$S |
| m-(i)C$_3$H$_7$O | H | H | CH$_3$S |
| m-(i)C$_3$H$_7$O | 4-F | H | CH$_3$S |
| m-(i)C$_3$H$_7$O | 4-CF$_3$ | H | CH$_3$S |
| m-(i)C$_3$H$_7$O | 3-F | H | CH$_3$S |
| m-(i)C$_3$H$_7$O | 3-CF$_3$ | H | CH$_3$S |
| m-(i)C$_3$H$_7$O | 4-Cl | H | CH$_3$S |
| m-(i)C$_3$H$_7$O | 4-CH$_3$ | H | CH$_3$S |
| m-(sec)C$_4$H$_9$O | H | H | CH$_3$S |
| m-(sec)C$_4$H$_9$O | 4-F | H | CH$_3$S |
| m-(sec)C$_4$H$_9$O | 4-CF$_3$ | H | CH$_3$S |
| m-(sec)C$_4$H$_9$O | 3-F | H | CH$_3$S |
| m-(sec)C$_4$H$_9$O | 3-CF$_3$ | H | CH$_3$S |
| m-(sec)C$_4$H$_9$O | 4-Cl | H | CH$_3$S |
| m-(sec)C$_4$H$_9$O | 4-CH$_3$ | H | CH$_3$S |
| m-CF$_3$O | H | H | CH$_3$S |
| m-CF$_3$O | 4-F | H | CH$_3$S |
| m-CF$_3$O | 4-CF$_3$ | H | CH$_3$S |
| m-CF$_3$O | 3-F | H | CH$_3$S |
| m-CF$_3$O | 3-CF$_3$ | H | CH$_3$S |
| m-CF$_3$O | 4-Cl | H | CH$_3$S |
| m-CF$_3$O | 4-CH$_3$ | H | CH$_3$S |
| o-CF$_3$ | H | H | CH$_3$S |
| o-CF$_3$ | 4-F | H | CH$_3$S |
| o-CF$_3$ | 4-CF$_3$ | H | CH$_3$S |
| o-CF$_3$ | 3-F | H | CH$_3$S |
| o-CF$_3$ | 3-CF$_3$ | H | CH$_3$S |
| o-CF$_3$ | 4-Cl | H | CH$_3$S |
| o-CF$_3$ | 4-CH$_3$ | H | CH$_3$S |
| m-C$_2$H$_5$O | 4-F | H | CH$_3$S |
| m-C$_2$H$_5$O | 4-CF$_3$ | H | CH$_3$S |
| m-F | 3-F | 4-F | CH$_3$S |
| m-Cl | 3-F | 4-F | CH$_3$S |
| m-CF$_3$ | 3-F | 4-F | CH$_3$S |
| m-(i)C$_3$H$_7$O | 3-F | 4-F | CH$_3$S |
| m-(sec)C$_4$H$_9$O | 3-F | 4-F | CH$_3$S |
| m-CF$_3$O | 3-F | 4-F | CH$_3$S |
| m-CH$_3$CH$_2$O | 3-F | 4-F | CH$_3$S |
| H | 4-Br | H | CH$_3$S |
| m-I | 4-CF$_3$ | H | CH$_3$S |
| m-I | 4-F | H | CH$_3$S |
| m-I | 2-F | 4-F | CH$_3$S |
| m-I | 2-F | 4-CF$_3$ | CH$_3$S |
| m-I | 3-F | 4-F | CH$_3$S |
| m-I | 3-F | 5-F | CH$_3$S |
| m-Cl | 2-F | 4-F | CH$_3$S |
| m-Cl | 2-F | 4-CF$_3$ | CH$_3$S |
| m-Cl | 3-F | 5-F | CH$_3$S |
| m-F | 4-Br | H | CH$_3$S |
| m-F | 2-F | 4-F | CH$_3$S |
| m-F | 3-F | 5-F | CH$_3$S |
| m-F | 2-F | 4-CF$_3$ | CH$_3$S |
| H | 2-F | 4-CF$_3$ | CH$_3$S |
| H | 3-F | 4-F | CH$_3$S |
| H | 3-F | 5-F | CH$_3$S |
| m-CF$_3$ | 2-F | 4-F | CH$_3$S |
| m-CF$_3$ | 2-F | 4-CF$_3$ | CH$_3$S |
| m-CF$_3$ | 3-F | 5-F | CH$_3$S |
| m-CF$_3$O | 2-F | 4-F | CH$_3$S |
| m-CF$_3$O | 2-F | 4-CF$_3$ | CH$_3$S |
| m-CF$_3$O | 3-F | 5-F | CH$_3$S |
| m-CF$_2$BrO | 4-F | H | CH$_3$S |
| m-CF$_2$BrO | 4-CF$_3$ | H | CH$_3$S |
| m-CF$_2$BrCF$_2$O | 4-F | H | CH$_3$S |
| m-CF$_2$BrCF$_2$O | 4-CF$_3$ | H | CH$_3$S |

PRODUCTION EXAMPLE 8 (Procedure (a))

6 g of 1-(3-trifluoromethylbenzoyl)-1-methane-sulfonyl-2-(N,N-dimethylamino)ethene and 4 g of 4-fluorobenzamidine hydrochloride were dissolved in 30 ml of methanol at room temperature. After adding 1.2 g of sodium methoxide thereto, the mixture was heated under reflux for 1 hour. The solvent was distilled away under reduced pressure. The residue was washed with water, and then dried to obtain 6 g of 2-(4-fluorophenyl)-4-(3-trifluoromethylphenyl)-5-methanesulfonylpyrimidine (Compound 112).

PRODUCTION EXAMPLE 9 ( Procedure (a))

6 g of 1-(3-trifluoromethylbenzoyl)-1-methanesulfonyl-2-(N,N-dimethylamino)ethene and 4.6 g of 2,4-difluorobenzamidine hydrochloride were dissolved in 30 ml of methanol at room temperature and 1.2 g of sodium methoxide was added thereto. The resulting mixture was heated under reflux for an hour. The solvent was distilled away under reduced pressure. The residue was washed with water and then dried to obtain 6 g of 2-(2,4-difluorophenyl)-4-(3-trifluoromethylphenyl)-5-meth anesulfonylpyrimidine (Compound 147).

PRODUCTION EXAMPLE 10 (Procedure (c))

1.5 g of 2-(4-chlorophenyl)-4-(3-trifluoromethylphenyl)-5-methylmercaptopyrimidine was added to 30 ml of dichloromethane. 2.0 g of m-chloroperbenzoic acid was added to the obtained reaction mixture under cooling in an ice-bath. Then, the resulting mixture was stirred at room temperature for 5 hours. After adding water, the mixture was extracted with dichloromethane. The organic phase was successively washed with a saturated aqueous solution of sodium sulfite and a saturated aqueous solution of sodium hydrogencarbonate. The solvent was distilled away under reduced pressure and the residue was subjected to column chromatography. Thus 1.5 g of 2-(4-chlorophenyl)-4-(3-trifluoromethylphenyl)-5-methanesulfonylpyrimidine was obtained (Compound 113).

PRODUCTION EXAMPLE 11 (Procedure (d))

2.8 g of 1-methylmercapto-1-(3-trifluoromethylbenzoyl)-2-(N,N-dimethylamino)ethene, 2.3 g of 4-chlorobenzamidine acetate and 650 mg of sodium methoxide were added to 200 ml of methanol and the resulting mixture was allowed to react under reflux for 5 hours. After completion of the reaction, the solvent was distilled away under reduced pressure. After adding water, the residue was extracted with ethyl acetate and subjected to column chromatography. Thus 2.5 g of 2-(4-chlorophenyl)-4-(3-trifluoromethylphenyl)-5-methylme rcaptopyrimidine was obtained (Compound 150).

Table 4 illustrates examples of the compound (II) produced according to the Production Example 8 to 11.

TABLE 4

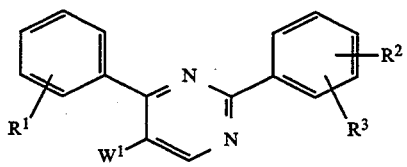

| Compound No. | R¹ | R² | R³ | W¹ | $^1$H-NMR (δ value)* |
|---|---|---|---|---|---|
| 101 | H | 4-CF₃ | H | CH₃SO₂ | 9.55(s, 1H), 8.72–8.6(d, 2H), 8.05–7.5(m, 7H), 3.15(s, 3H) |
| 102 | H | 4-NO₂ | H | CH₃SO₂ | 9.45(s, 1H), 8.8–8.3(q, 4H), 7.7(brs, 5H), 3.2(s, 3H) |
| 103 | m-Cl | H | H | CH₃SO₂ | 9.45(s, 1H), 8.65–8.45(m, 2H), 7.8–7.45(m, 7H), 2.8(s, 3H) |
| 104 | m-Cl | 4-CF₃ | H | CH₃SO₂ | 9.5(s, 1H), 8.7–8.55(d, 2H), 7.85–7.2(m, 6H), 2.8(s, 3H) |
| 105 | m-Br | H | H | CH₃SO₂ | 9.25(s, 1H), 8.55–7.3(m, 9H), 3.15(s, 3H) |
| 106 | m-Br | 4-Cl | H | CH₃SO₂ | 9.45(s, 1H), 8.55–7.5(m, 8H), 3.2(s, 3H) |
| 107 | m-Br | 4-Br | H | CH₃SO₂ | 9.5(s, 1H), 8.5–8.35(d, 2H), 7.95–7.4(m, 6H), 3.2(s, 3H) |
| 108 | m-Br | 4-CF₃ | H | CH₃SO₂ | 9.45(s, 1H), 8.7–8.5(d, 2H), 8.0–7.4(m, 6H), 3.2(s, 3H) |
| 109 | o-Br | 4-CF₃ | H | CH₃SO₂ | 9.55(s, 1H), 8.65–8.5(d, 2H), 7.95–7.35(m, 6H), 3.2(s, 3H) |
| 110 | m-CF₃ | H | H | CH₃SO₂ | 9.5(s, 1H), 8.65–7.4(m, 9H), 2.8(s, 3H) |
| 111 | m-CF₃ | 4-CH₃ | H | CH₃SO₂ | 9.45(s, 1H), 8.5–8.35(d, 2H), 8.05–7.85(m, 4H), 7.45–7.3(d, 2H), 3.15(s, 3H), 2.4(s, 3H) |
| 112 | m-CF₃ | 4-F | H | CH₃SO₂ | 9.45(s, 1H), 8.70–7.0(m, 8H), 3.0(s, 3H) |
| 113 | m-CF₃ | 4-Cl | H | CH₃SO₂ | 9.4(s, 1H), 8.55–8.4(d, 2H), 8.0–7.45(m, 6H), 3.0(s, 3H) |
| 114 | m-CF₃ | 4-Br | H | CH₃SO₂ | 9.45(s, 1H), 8.5–7.6(m, 8H), 3.05(s, 3H) |
| 115 | m-CF₃ | 4-CF₃ | H | CH₃SO₂ | 9.5(s, 1H), 8.75–7.6(m, 8H), 2.8(s, 3H) |
| 116 | m-CF₃ | 4-NO₂ | H | CH₃SO₂ | 9.6(s, 1H), 8.8–7.7(m, 8H), 3.25(s, 3H) |
| 117 | m-CF₃ | 4-CH₃O | H | CH₃SO₂ | 9.4(s, 1H), 8.6–8.4(d, 2H), 8.1–7.7(m, 4H), 7.1–6.95(d, 2H), 3.9(s, 3H), 3.0(s, 3H) |
| 118 | m-I | 4-CF₃ | H | CH₃SO₂ | 9.5(s, 1H), 8.75–8.6(d, 2H), 8.15–7.2(m, 6H), 3.22(s, 3H) |
| 119 | m-F | H | H | CH₃SO₂ | 9.45(s, 1H), 8.55–8.35(m, 2H), 7.75–7.55(m, 7H), 3.1(s, 3H) |
| 120 | m-F | 4-CH₃ | H | CH₃SO₂ | 9.35(s, 1H), 8.4–8.25(d, 2H), 7.6–7.3(m, 6H), 3.2(s, 3H), 2.45(s, 3H) |
| 121 | m-F | 4-F | H | CH₃SO₂ | 9.4(s, 1H), 8.65–8.4(m, 2H), 7.75–7.0(m, 6H), 2.8(s, 3H) |
| 122 | m-F | 4-Cl | H | CH₃SO₂ | 9.35(s, 1H), 8.5–8.35(d, 2H), 7.7–7.5(m, 6H), 3.2(s, 3H) |
| 123 | m-F | 4-Br | H | CH₃SO₂ | 9.35(s, 1H), 8.4–8.25(d, 2H), 7.75–7.4(m, 6H), 3.15(s, 3H) |
| 124 | m-I | 4-F | H | CH₃SO₂ | 9.35(s, 1H), 8.6–8.3(m, 2H), 8.0–7.15(m, 6H), 3.05(s, 3H) |
| 125 | m-CF₃O | 4-CF₃ | H | CH₃SO₂ | 9.45(s, 1H), 8.7–8.55(d, 2H), 7.8–7.45(m, 6H), 2.8(s, 3H) |
| 126 | m-CF₃O | 4-F | H | CH₃SO₃ | 9.45(s, 1H), 8.7–8.45(m, 2H), 7.75–7.0(m, 6H), 2.8(s, 3H) |
| 127 | o-CF₃ | 4-CF₃ | H | CH₃SO₂ | 9.45(s, 1H), 8.7–8.55(m, 2H), 7.8–7.65(m, 6H), 2.8(s, 3H) |
| 128 | m-CH₃ | 4-F | H | CH₃SO₂ | 9.30(s, 1H), 8.6–6.9(m, 8H), 2.65(s, 3H), 2.4(s, 3H) |
| 129 | m-C₂H₅O | 4-F | H | CH₃SO₂ | 9.40(s, 1H), 8.70–8.40(m, 2H), 7.50–6.95(m, 6H), 4.30–3.95(q, 2H), 2.75(s, 3H), 1.60–1.35(t, 3H) |
| 130 | m-CH₃OCH₂O | 4-F | H | CH₃SO₂ | 9.35(s, 1H), 8.60–8.35(m, 2H), 7.45–6.95(m, 6H), 5.20(s, 2H), 3.45(s, 3H), 2.75(s, 3H) |
| 131 | m-CF₃ | 2-F | H | CH₃SO₂ | 9.50(s, 1H), 8.30–7.0(m, 8H), 2.80(s, 3H) |
| 132 | m-C₆H₅O | 4-F | H | CH₃SO₂ | 9.35(s, 1H), 8.60–8.35(m, 2H), 7.5–6.95(m, 11H), 2.80(s, 3H) |
| 133 | o-CF₃ | 2-F | H | CH₃SO₂ | 9.5(s, 1H), 8.20–7.0(m, 8H), 2.80(s, 3H) |
| 134 | m-Cl | 2-F | H | CH₃SO₂ | 9.50(s, 1H), 8.35–7.0(m, 8H), 2.80(s, 3H) |
| 135 | m-CF₃ | 3-CH₃O | H | CH₃SO₂ | 9.40(s, 1H), 8.20–6.95(m, 8H), 3.85(s, 3H), 2.75(s, 3H) |
| 136 | m-CF₃ | 3-F | H | CH₃SO₂ | 9.45(s, 1H), 8.40–7.05(m, 8H), 2.80(s, 3H) |
| 137 | m-CF₃ | 3-CF₃ | H | CH₃SO₂ | 9.45(s, 1H), 8.85–8.60(m, 2H), 8.10–7.40(m, 6H), 2.75(s, 3H) |
| 138 | m-CF₃O | 3-CF₃ | H | CH₃SO₂ | 9.30(s, 1H), 8.70–8.50(m, 2H), 7.80–7.20(m, 6H), 2.90(s, 3H) |
| 139 | m-CH₃OCH₂O | 4-CF₃ | H | CH₃SO₂ | 9.50(s, 1H), 8.80–8.50(m, 2H), 7.85–7.20(m, 6H), 5.25(s, 2H), 3.50(s, 3H), 2.80(s, 3H) |
| 140 | m-CF₃O | 3-Cl | H | CH₃SO₂ | 9.40(s, 1H), 8.60–8.35(m, 2H), 7.90–7.25(m, 6H), 2.75(s, 3H) |
| 141 | m-CF₃ | 4-SCH₃ | H | CH₃SO₂ | 9.30(s, 1H), 8.45–7.15(m, 8H), 2.75(s, 3H), 2.50(s, 3H) |
| 142 | m-CH₃CH₂O | 4-CF₃ | H | CH₃SO₂ | 9.35(s, 1H), 8.60–8.45(m, 2H), 7.70–6.95(m, 6H), 4.25–3.90(q, 2H), 2.75(s, 3H), 1.55–1.30(t, 3H) |
| 143 | m-CN | 4-CF₃ | H | CH₃SO₂ | 9.40(s, 1H), 8.75–7.6(m, 8H), 3.0(s, 3H) |
| 144 | o-CF₃O | 2-F | 4-F | CH₃SO₂ | 9.40(s, 1H), 8.45–6.70(m, 7H), 2.80(s, 3H) |
| 145 | m-CF₃O | 3-F | 4-F | CH₃SO₂ | 9.35(s, 1H), 8.45–7.40(m, 7H), 3.10(s, 3H) |
| 146 | m-CF₃O | 3-F | 5-F | CH₃SO₂ | 9.35(s, 1H), 8.20–7.10(m, 7H), 2.60(s, 3H) |
| 147 | m-CF₃ | 2-F | 4-F | CH₃SO₂ | 9.45(s, 1H), 8.45–6.70(m, 7H), 2.75(s, 3H) |
| 148 | m-CF₃ | 3-F | 4-F | CH₃SO₂ | 9.50(s, 1H), 8.55–7.05(m, 7H), 2.75(s, 3H) |

TABLE 4-continued

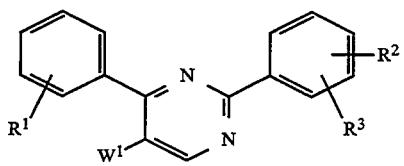

| Compound No. | $R^1$ | $R^2$ | $R^3$ | $W^1$ | $^1$H-NMR ($\delta$ value)* |
|---|---|---|---|---|---|
| 149 | m-$CF_3$ | 3-F | 5-F | $CH_3SO_2$ | 9.45(s, 1H), 8.25–6.75(m, 7H), 2.75(s, 3H) |
| 150 | m-$CF_3$ | 4-Cl | H | $CH_3S$ | 8.7–7.2(m, 9H), 2.5(s, 3H) |
| 151 | o-$CF_3$ | 4-Cl | H | $CH_3S$ | 8.75–7.25(m, 9H), 2.5(s, 3H) |

*Solvent
$CDCl_3$: Compounds 104, 110, 112, 121, 125, 126, 127, 129 to 141
$CDCl_3$ + DMSO-$d_6$: Compounds 113, 117, 128, 142 to 151
DMSO-$d_6$: other compounds Examples of the compounds (VIII) {(VIII-1), (VIII-2) and (VIII-3)} which can be produced by the procedures (b), (e), (f) include those shown in Table 5. However, it is a matter of course that the present invention is not restricted thereby.

TABLE 5

| $R^1$ | $W^2$ |
|---|---|
| H | $SCOOCH_3$ |
| H | $SCOOC_2H_5$ |
| m-F | $SCOOCH_3$ |
| m-F | $SCOOC_2H_5$ |
| m-Cl | $SCOOCH_3$ |
| m-Cl | $SCOOC_2H_5$ |
| m-Br | $SCOOCH_3$ |
| m-Br | $SCOOC_2H_5$ |
| m-$CF_3$ | $SCOOCH_3$ |
| m-$CF_3$ | $SCOOC_2H_5$ |
| m-$CH_3O$ | $SCOOCH_3$ |
| m-$CH_3O$ | $SCOOC_2H_5$ |
| m-$C_2H_5O$ | $SCOOCH_3$ |
| m-$C_2H_5O$ | $SCOOC_2H_5$ |

| $R^{11}$ | $R^5$ |
|---|---|
| m-(i)$C_3H_7O$ | $SCOOCH_3$ |
| m-(i)$C_3H_7O$ | $SCOOC_2H_5$ |
| m-(sec)$C_4H_9O$ | $SCOOCH_3$ |
| m-(sec)$C_4H_9O$ | $SCOOC_2H_5$ |
| m-$CH_3$ | $SCOOCH_3$ |
| o-$CH_3$ | $SCOOCH_3$ |
| m-$CF_3O$ | $SCOOCH_3$ |
| m-$CF_3O$ | $SCOOC_2H_5$ |
| o-Br | $SCOOCH_3$ |
| o-Br | $SCOOC_2H_5$ |
| o-$CF_3$ | $SCOOCH_3$ |
| o-$CF_3$ | $SCOOC_2H_5$ |
| m-$CF_3O$ | $SCOOC_3H_7$ |
| m-$CF_3$ | $SCOOC_3H_7$ |
| m-$C_6H_5O$ | $SCOOCH_3$ |
| m-$CH_3OCH_2O$ | $SCOOCH_3$ |
| m-I | $SCOOCH_3$ |
| m-$CF_2ClO$ | $SCOOCH_3$ |
| m-$CF_3CF_2O$ | $SCOOCH_3$ |
| m-$CF_2BrO$ | $SCOOCH_3$ |
| m-$CF_2BrCF_2O$ | $SCOOCH_3$ |
| H | $SCH_3$ |
| m-F | $SCH_3$ |
| m-Cl | $SCH_3$ |
| m-Br | $SCH_3$ |
| m-$CF_3$ | $SCH_3$ |

TABLE 5-continued

| | |
|---|---|
| m-$CH_3O$ | $SCH_3$ |
| m-$C_2H_5O$ | $SCH_3$ |
| m-(i)$C_3H_7O$ | $SCH_3$ |
| m-(sec)$C_4H_9O$ | $SCH_3$ |
| m-$CF_3O$ | $SCH_3$ |
| o-Br | $SCH_3$ |
| o-$CF_3$ | $SCH_3$ |
| m-$CH_3$ | $SCH_3$ |
| m-$C_6H_5O$ | $SCH_3$ |
| m-$CH_3OCH_2O$ | $SCH_3$ |
| m-I | $SCH_3$ |
| m-$CF_2ClO$ | $SCH_3$ |
| m-$CF_3CF_2O$ | $SCH_3$ |
| m-$CF_2BrO$ | $SCH_3$ |
| m-$CF_2BrCF_2O$ | $SCH_3$ |

PRODUCTION EXAMPLE 12 (Procedure (b))

2.5 g of m-trifluoromethyl-α-methanesulfonylacetophenone and 1.4 g of N,N-dimethylformamide dimethylacetal were dissolved in 40 ml of toluene, and the resulting mixture was heated under reflux for 2 hours. The solvent was distilled away under reduced pressure. The residue was treated with column chromatography on silica gel, thereby obtaining 3 g of 1-(3-trifluoromethylbenzoyl)-1-methanesulfonyl-2-(N,N-dimethylamino)ethene (Compound 205).

PRODUCTION EXAMPLE 13 (Procedure (f))

4.2 g of 1-(N,N-dimethylamino)-2-(2-trifluoromethylbenzoyl)ethene and 2.6 g of triethylamine were added to 50 ml of benzene. 2.4 g of methoxycarbonylsulfenyl chloride dissolved in 10 ml of benzene was added dropwise to the solution obtained above under cooling in an ice-bath. After completion of the addition, the reaction mixture was stirred at room temperature for 1 hour. After completion of the reaction, the solvent was distilled away under reduced pressure. After adding an aqueous solution of sodium hydrogencarbonate, the mixture was extracted with ether. Thus 5.0 g of 1-methoxycarbonylthio-1-(2-trifluoromethylbenzoyl)-2-

(N,N-dimethylamino)ethene was obtained (Compound 209).

PRODUCTION EXAMPLE 14 (Procedure (e))

5.8 g of 1-methoxycarbonylthio-1-(2-trifluoromethylbenzoyl)-2-(N,N-dimethylamino)ethene and 4.2 g of methyl iodide were added to 100 ml of ethanol. 770 mg of sodium hydroxide was added to the obtained mixture under cooling in an ice-bath. Then the resulting mixture was stirred at room temperature for 3 hours and then neutralized by adding acetic acid.

The solvent was distilled away and water was added to the residue. The mixture was extracted with ethyl acetate and subjected to column chromatography. Thus 4.5 g of 1-methylmercapto-1-(2-trifluoromethylbenzoyl)-2-(N,N-dimethylamino)ethene was obtained (Compound 216).

Some examples of the compound produced by the Production Examples 12 to 14 are shown in Table 6.

TABLE 6

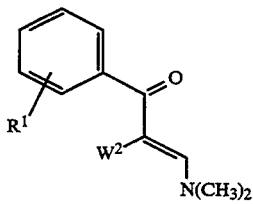

| Compound No. | $R^1$ | $W^2$ | $^1$H—NMR (δ value)* |
|---|---|---|---|
| 201 | m-F | $SO_2CH_3$ | 7.8(s, 1H), 7.7–7.2(m, 4H), 3.2(s, 3H), 2.8(brs, 6H) |
| 202 | m-Cl | $SO_2CH_3$ | 7.7–7.1(m, 5H), 3.05(s, 3H), 2.7(brs, 6H) |
| 203 | m-Br | $SO_2CH_3$ | 7.9–7.15(m, 5H), 3.15(s, 3H), 2.75(brs, 6H) |
| 204 | m-I | $SO_2CH_3$ | 8.15–7.1(m, 5H), 3.2(s, 3H), 2.8(brs, 6H) |
| 205 | m-$CF_3$ | $SO_2CH_3$ | 8.0–7.5(m, 5H), 3.15(s, 3H), 2.8(brs, 6H) |
| 206 | o-Br | $SO_2CH_3$ | 7.85–7.25(m, 5H), 3.0(brs, 9H) |
| 207 | m-$CF_3$O | $SO_2CH_3$ | 7.80–7.40(m, 5H), 3.15(s, 3H), 2.75(brs, 6H) |
| 208 | m-$CH_3OCH_2O$ | $SO_2CH_3$ | 7.70(s, 1H), 7.40–7.10(m, 4H), 5.15(s, 2H), 3.40(s, 3H), 3.15(s, 3H), 2.7(brs, 6H) |
| 209 | o-$CF_3$ | $SCO_2CH_3$ | 7.65–7.15(m. 5H) 3,70(s, 3H), 3.15(s, 6H) |
| 210 | m-$CF_3$ | $SCO_2CH_3$ | 7.75–7.45(m, 5H), 3.75 s, 3H), 3.25(s, 6H) |
| 211 | m-Cl | $SCO_2CH_3$ | 7.70–7.20(m, 5H), 3.75(s, 3H), 3.20(s, 6H) |
| 212 | H | $SCO_2CH_3$ | 7.70–7.25(m, 6H), 3.80(s, 3H), 3.20(s, 6H) |
| 213 | m-$CH_3O$ | $SCO_2CH_3$ | 7.65(s, 1H), 7.35–6.85(m, 4H) 3.75(s, 6H), 3.20(s, 6H) |
| 214 | H | $SCH_3$ | 7.4(m, 6H), 3.25(s, 6H), 2.1(s, 3H) |
| 215 | m-$CF_3$ | $SCH_3$ | 7.8–7.2(m, 6H), 3.25(s, 6H), 2.05(s, 3H) |
| 216 | o-$CF_3$ | $SCH_3$ | 7.7–7.1(m, 6H), 3.25(s, 6H), 2.05(s, 3H) |
| 217 | m-Cl | $SCH_3$ | 7.75–7.15(m, 6H), 3.3(s, 6H), 2.05(s, 3H) |

*Solvent: $CDCl_3$
**Solvent: $CDCl_3$ + DMSO-$d_6$

For the practical use of the compound (I), it is usually formulated with conventional solid or liquid carriers or diluents as well as surface active agents or auxiliary agents into conventional preparation forms such as emulsifiable concentrates, wettable powders, suspensions and granules. The content of the compound (I) as the active ingredient in such preparation forms is normally within a range of about 1 to 80% by weight, preferably of about 2 to 70% by weight. Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrous silicate, etc. As the liquid carrier or diluent, there may be exemplified aromatic hydrocarbons (e.g., xylene, methylnaphthalene), alcohols (e.g., isopropanol, ethylene glycol, cellosolve ), ketones (e.g., acetone, cyclohexanone, isophorone ), soybean oil, cotton seed oil, dimethyl sulfoxide, N,N-dimethylformamide, acetonitrile, water, etc.).

The surface active agent used for emulsification, dispersion or spreading may be of any type, for instance, either cationic, anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene-polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl-acid phosphate), etc.

Practical embodiments of the herbicidal composition according to the present invention are illustratively shown in the following Formulation Examples wherein parts are by weight. The compound number of the active ingredient corresponds to the one in Table 2.

FORMULATION EXAMPLE 1

Seventy parts of Compound 8 or 17, 3 parts of calcium ligninsulfonate, 2 parts of sodium laurylsulfate and 25 parts of synthetic hydrous silicate are well mixed while being powdered to obtain a wettable powder.

FORMULATION EXAMPLE 2

Ten parts of Compound 10, 18, or 20, 14 parts of polyoxyethylene styrylphenyl ether, 6 parts of calcium dodecylbenzenesulfonate, 70 parts of xylene are well mixed to obtain an emulsifiable concentrate.

FORMULATION EXAMPLE 3

Two parts of Compound 12 or 23, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound 20 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

The compound (I) thus formulated in any suitable preparation form is useful for pre-emergence or post-emergence control of undesired weeds by soil or foliar treatment as well as flood following treatment. These treatments include application to the soil surface prior to or after transplanting, incorporation into the soil, etc.

The foliar treatment may be effected by spraying the herbicidal composition containing the compound (I) over the top of plants. It may also be applied directly to the weeds if care is taken to keep the chemical off the crop foliage.

The compound (I) may be used together with any other herbicide to improve its activity as a herbicide, and in some cases, a synergistic effect can be expected. Further, it may be applied in combination with an insecticide, and acaricide, a nematocide, a fungicide, a plant growth regulator, a fertilizer, a soil improver, etc. Furthermore, it may be used as a herbicide applicable to agricultural plowed fields as well as paddy fields. It is also useful as a herbicide to be employed for orchards, pasture lands, lawns, forests, non-agricultural fields, etc.

The dosage of the compound (I) may vary depending on the prevailing weather conditions, the formulation used, the prevailing season, the mode of application, the soil involved, the crop and weed species, etc. Generally, however, the dosage of the active ingredient is from about 1 to 8000 grams, preferably from about 5 to 2000 grams per hectare.

The herbicidal composition of the invention formulated in the form of an emulsifiable concentrate, a wettable powder or a suspension may ordinarily be employed by diluting it with water at a volume of about 100 to 1000 liters per hectare, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the compound (I) as herbicides will be illustratively shown in the following Test Examples wherein the phytotoxicity to crop plants and the herbicidal activity on weeds were observed visually as to the degree of germination as well as the growth inhibition and rated with an index 0, 1, 2, 3, 4, 5, 6, 7, 8, 9, or 10, the numeral "0" indicating no material difference as seen in comparison with the untreated plants and the numeral "10" indicating the complete inhibition or death of the test plants.

The compounds as shown in Table 7 were used for comparison.

TABLE 7

| Compound Code | Structural Formula | Remarks |
|---|---|---|
| A | | Metamitron (Commercial herbicide) |
| B | | DSMA (Commercial herbicide) |
| C | | Benthiocarb (Commercial herbicide) |

TABLE 7-continued

| Compound Code | Structural Formula | Remarks |
|---|---|---|
| D | | Described in J. Heterocyclic Chem., 23, 77 (1986) |

TEST EXAMPLE 1

Cylindrical plastic pots (diameter, 10 cm; height, 10 cm) were filled with upland field soil, and the seeds of tall morningglory and velvetleaf were sowed therein and covered with soil. A designated amount of the test compound formulated in a wettable powder as in Formulation Example 1 was diluted with water, and the dilution was sprayed onto the soil surface by means of a small hand sprayer at a spray volume of 1000 liters per hectare. The test plants were grown in a greenhouse for 20 days, and the herbicidal activity was examined. The results are shown in Table 8.

TABLE 8

| Compound No. | Dosage (g/ha) | Herbicidal Activity Tall Morningglory | Velvetleaf |
|---|---|---|---|
| 8 | 2000 | 10 | 10 |
| 12 | 2000 | 10 | — |
| 16 | 2000 | 10 | 10 |
| 17 | 2000 | 10 | 9 |
|  | 500 | 10 | — |
| 18 | 2000 | 9 | 10 |
|  | 500 | — | 10 |
| 19 | 8000 | 10 | 10 |
| 21 | 2000 | 10 | 10 |
| 31 | 2000 | 10 | 10 |
|  | 500 | 10 | — |
| 32 | 2000 | 10 | 10 |
| 34 | 2000 | 10 | 9 |
|  | 500 | 10 | — |
| 58 | 2000 | 10 | — |
| 61 | 2000 | 9 | — |
| 65 | 2000 | 10 | — |
| 74 | 2000 | 9 | — |
| 75 | 2000 | 9 | 8 |
| 76 | 2000 | 10 | — |
| 77 | 2000 | 10 | — |
| 78 | 2000 | 10 | 9 |
| A | 8000 | 6 | 6 |
|  | 2000 | 2 | 2 |
| D | 2000 | 0 | 0 |

TEST EXAMPLE 2

Cylindrical plastic pots (diameter, 10 cm; height, 10 cm) were filled with upland field soil, and the seeds of tall morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 1000 liters per hectare. The test plants were further grown in a greenhouse for 20 days, and the herbicidal activity was examined. The results are shown in Table 9.

TABLE 9

| Compound No. | Dosage (g/ha) | Herbicidal Activity Radish | Velvetleaf | Tall Morningglory |
|---|---|---|---|---|
| 2 | 500 | 8 | 8 | 9 |
| 6 | 2000 | 10 | 10 | 10 |
|   | 500 | 9 | — | — |
| 7 | 2000 | 10 | 10 | 10 |
|   | 500 | 9 | 9 | — |
| 8 | 2000 | 10 | 10 | 10 |
|   | 500 | 10 | 9 | 10 |
| 9 | 500 | 10 | 10 | 10 |
|   | 125 | 8 | — | 10 |
| 10 | 500 | 9 | 9 | 10 |
|   | 125 | 9 | 9 | 9 |
|   | 32 | 9 | — | 9 |
| 11 | 500 | — | 9 | 9 |
| 12 | 500 | 10 | 10 | 10 |
|   | 125 | 9 | 9 | 10 |
|   | 32 | — | 8 | 10 |
| 14 | 2000 | 9 | 10 | 9 |
| 16 | 500 | 10 | 9 | 10 |
|   | 125 | 8 | 8 | 10 |
| 17 | 500 | 8 | 9 | 10 |
|   | 125 | — | 9 | 10 |
| 18 | 500 | 10 | 10 | 10 |
|   | 125 | 10 | 10 | 10 |
|   | 32 | 10 | 9 | 9 |
| 19 | 2000 | 9 | 9 | 10 |
|   | 500 | 9 | 9 | 10 |
| 20 | 500 | 10 | 9 | 10 |
|   | 125 | 9 | 9 | 9 |
|   | 32 | 9 | 8 | 9 |
| 21 | 500 | 10 | 9 | 9 |
|   | 125 | 10 | 9 | 9 |
|   | 32 | 10 | 9 | 9 |
| 23 | 500 | 10 | 8 | 10 |
|   | 125 | 9 | 8 | 9 |
| 31 | 500 | 10 | 10 | 9 |
|   | 125 | 10 | 9 | 9 |
|   | 32 | 10 | 9 | 9 |
| 32 | 500 | 10 | 9 | 10 |
|   | 125 | 10 | 9 | 10 |
|   | 32 | 10 | 9 | 9 |
| 34 | 500 | 10 | 9 | 10 |
|   | 125 | 9 | 9 | 10 |
| 47 | 2000 | 10 | 10 | 10 |
|   | 500 | 9 | 10 | 10 |
|   | 125 | 9 | 10 | 9 |
| 48 | 2000 | 10 | 9 | 10 |
|   | 500 | 10 | 9 | 10 |
|   | 125 | 10 | 9 | 10 |
| 49 | 2000 | 10 | 10 | 10 |
|   | 500 | 10 | 9 | 10 |
|   | 125 | 10 | 9 | 10 |
| 52 | 2000 | 9 | — | 9 |
| 58 | 2000 | 10 | 9 | 10 |
|   | 500 | 9 | 9 | 10 |
| 60 | 2000 | 9 | 9 | — |
|   | 500 | 9 | 9 | — |
| 61 | 500 | 10 | 9 | 10 |
|   | 125 | 9 | 9 | 10 |
|   | 32 | 9 | 8 | 10 |
| 62 | 500 | 9 | 9 | 10 |
|   | 125 | 9 | 9 | 9 |
| 63 | 500 | 9 | 8 | 10 |
|   | 125 | 9 | 8 | 9 |
|   | 32 | 9 | 8 | 9 |
| 64 | 2000 | 9 | 9 | 9 |
|   | 500 | 9 | 9 | 9 |
| 65 | 500 | 10 | 9 | 10 |
|   | 125 | 10 | 9 | 10 |
|   | 32 | 10 | 9 | 10 |
| 66 | 500 | 9 | 9 | 10 |
|   | 125 | 9 | 9 | 10 |
|   | 32 | 9 | 9 | 9 |
| 74 | 2000 | 9 | 9 | 9 |
|   | 500 | 10 | 9 | 10 |
|   | 125 | 10 | — | 9 |
| 75 | 2000 | 10 | 9 | 10 |
|   | 500 | 10 | 9 | 10 |
|   | 125 | 9 | 9 | 10 |

TABLE 9-continued

| Compound No. | Dosage (g/ha) | Herbicidal Activity Radish | Velvetleaf | Tall Morningglory |
|---|---|---|---|---|
| 76 | 2000 | 10 | 10 | 10 |
|   | 500 | 9 | 10 | 10 |
|   | 125 | — | 10 | 10 |
| 77 | 2000 | 10 | 9 | 9 |
|   | 500 | 10 | 8 | 9 |
|   | 125 | 10 | 8 | 9 |
| 78 | 2000 | 10 | 9 | — |
|   | 500 | 10 | 9 | 10 |
|   | 125 | 10 | 8 | 9 |
| 79 | 2000 | 8 | 10 | 10 |
|   | 500 | — | 10 | 10 |
|   | 125 | — | 8 | 10 |
| B | 8000 | 9 | 0 | 0 |
|   | 2000 | 8 | 0 | 0 |
| D | 2000 | 3 | 2 | — |

TEST EXAMPLE 3

Cylindrical plastic pots (diameter, 8 cm; height, 12 cm) were filled with paddy field soil, and the seeds of barnyardgrass (*Echinochloa oryzicola*) were sowed in 1 to 2 cm depth, and water was poured therein to make a flooded condition.

Five days (at that time weeds began to germinate) thereafter, a designated amount of the test compound formulated in an emulsifiable concentrate as in Formulation Example 2 and diluted with water (5 ml) was applied to the pots by per fusion. The test plants were grown for an additional 20 days in a greenhouse, and the herbicidal activity was examined. The results are shown in Table 10.

TABLE 10

| Compound No. | Dosage (g/ha) | Herbicidal Activity Banyardgrass |
|---|---|---|
| 2 | 4000 | 10 |
| 4 | 4000 | 10 |
| 6 | 4000 | 10 |
| 7 | 4000 | 10 |
| 8 | 4000 | 10 |
| 9 | 4000 | 10 |
| 10 | 4000 | 10 |
| 11 | 4000 | 10 |
| 12 | 4000 | 10 |
| 13 | 4000 | 10 |
| 14 | 4000 | 10 |
| 15 | 4000 | 10 |
| 16 | 4000 | 10 |
| 17 | 4000 | 10 |
| 18 | 4000 | 10 |
| 19 | 4000 | 10 |
| 20 | 4000 | 10 |
| 21 | 4000 | 10 |
| 23 | 4000 | 10 |
| 31 | 4000 | 10 |
| 32 | 4000 | 10 |
| 34 | 4000 | 10 |
| 47 | 4000 | 10 |
| 48 | 4000 | 10 |
| 49 | 4000 | 10 |
| 52 | 4000 | 10 |
| 58 | 4000 | 10 |
| 61 | 4000 | 10 |
| 62 | 4000 | 10 |
| 64 | 4000 | 10 |
| 65 | 4000 | 10 |
| 66 | 4000 | 10 |
| 74 | 4000 | 10 |
| 75 | 4000 | 10 |
| 76 | 4000 | 10 |
| 77 | 4000 | 10 |
| 78 | 4000 | 10 |
| 79 | 4000 | 10 |

TABLE 10-continued

| Compound No. | Dosage (g/ha) | Herbicidal Activity Banyardgrass |
|---|---|---|
| D | 4000 | 0 |

TEST EXAMPLE 4

Wagner's pots (1/5000 are) were filled with paddy field soil, and the seeds of barnyardgrass (*Echinochloa oryzicola*), broad-leaved weeds (i.e., common falsepimpernel, indian toothcup, waterwort), water nutgrass and hardstem bulrush were sowed in 1 to 2 cm depth. Water was poured therein to make a flooded condition, and rice seedlings of 3-leaf stage and tubers of water nutgrass were transplanted therein, and the test plants were grown in a greenhouse. Five days (at that time barnyardgrass began to germinate) thereafter, a designated amount of the test compound formulated in an emulsifiable concentrate as in Formulation Example 2 and diluted with water (10 ml) was applied to the pots by perfusion. The test plants were grown for an additional 20 days in the greenhouse, and the herbicidal activity was examined. The results are shown in Table 11. At the time of the treatment, the depth of water in the pots was kept at 4 cm and following two days, water was let leak a volume corresponding to a 3 cm depth per day.

TABLE 11

| Compound No. | Dosage (g/ha) | Phytotoxicity Rice Plant | Herbicidal Activity Barnyardgrass | Broadleaved Weeds | Hardstem Bulrush | Water Nutgrass |
|---|---|---|---|---|---|---|
| 18 | 250 | 3 | 10 | 10 | 10 | 10 |
|    | 63  | 0 | 10 | 10 | 10 | 10 |
| 19 | 250 | 1 | 10 | 10 | 9  | 10 |
|    | 63  | 0 | 10 | 10 | 8  | 9  |
| 21 | 250 | 2 | 10 | 10 | 10 | 10 |
|    | 63  | 0 | 10 | 10 | 10 | 10 |
| C  | 250 | 0 | 4  | 0  | 0  | 0  |
|    | 63  | 0 | 0  | 0  | 0  | 0  |

TEST EXAMPLE 5

Vats (area: 33×23 cm$^2$, depth: 11 cm) were filled with field soil, and the seeds of soybean, corn, rice, velvetleaf, redroot pigweed, green foxtail and barnyardgrass were sowed therein and covered with soil of 1 to 2 cm in thickness. A designated amount of the test compound formulated in an emulsifiable concentrate as in Formulation Example 2 was diluted with water, and the dilution was sprayed onto the soil surface by means of a small hand sprayer at a spray volume of 1000 liters per hectare. The test plants were grown in a green house for 20 days, and then herbicidal activity and phytotoxicity were examined. The results are shown in Table 12.

TABLE 12

| Compound No. | Dosage (g/ha) | Phytotoxicity Soybean | Corn | Rice | Herbicidal Activity Velvetleaf | Redroot pigweed | Green Foxtail | Barnyardgrass |
|---|---|---|---|---|---|---|---|---|
| 18 | 250 | 2 | 0 | 1 | 10 | 10 | 10 | 9  |
|    | 125 | 0 | 0 | 0 | 8  | 10 | 10 | 8  |
| 31 | 250 | 1 | 2 | 1 | 10 | 10 | 10 | 10 |
|    | 125 | 0 | 0 | 0 | 9  | 10 | 10 | 9  |
| D  | 250 | 0 | 0 | 0 | 0  | 0  | 0  | 0  |

TEST EXAMPLE 6

Vats (area: 33×23 cm$^2$, depth: 11 cm) were filled with field soil, and seeds of wheat, common chickweed, persian speedwell, field pansy, annual bluegrass and blackgrass were sowed therein and covered with soil of 1 to 2 cm in thickness. A designated amount of the test compound formulated in an emulsifiable concentrate as in Formulation Example 2 was diluted with water, and the dilution was sprayed onto the soil surface by means of a small hand sprayer at a spray volume of 1000 liters per hectare. The test plants were grown in a green house for 27 days and then herbicidal activity and phytotoxicity were examined. The results are shown in Table 13.

TABLE 13

| Compound No. | Dosage (g/ha) | Phytotoxicity Wheat | Herbicidal Activity Common Chickweed | Persian Speedwell | Field Pansy | Annual Bluegrass | Blackgrass |
|---|---|---|---|---|---|---|---|
| 18 | 250 | 1 | 10 | 10 | 8 | 10 | 8 |
| 31 | 250 | 0 | 10 | 10 | 8 | 10 | 8 |
| D  | 250 | 0 | 0  | 0  | 0 | 0  | 0 |

TEST EXAMPLE 7

Vats (area: 33×23 cm$^3$, depth: 11 cm) were filled with field soil, and seeds of wheat, persian speedwell, wild mustard and field pansy were sowed therein and grown for 31 days. A designated amount of the test compound formulated in an emulsifiable concentrate as in Formulation Example 2 was diluted with water, and the dilution was uniformly sprayed onto the whole of the stems and leaves of the plants by means of a small hand sprayer at a spray volume of 1000 liters per hectare. The growth of weeds and crops varied depending upon a kind of plant. During the one to four leafstages, the height of these plants ranged from 3 to 25 cm. 25 days after the treatment, the herbicidal activity and phytotoxicity were examined. The results are shown in Table 14. The procedures were effected throughout the test period in a greenhouse.

TABLE 14

| Compound No. | Dosage (g/ha) | Phytotoxicity Wheat | Herbicidal Activity Persian Speedwell | Wild Mustard | Field Pansy |
|---|---|---|---|---|---|
| 31 | 250 | 1 | 10 | 9 | 9 |
|    | 125 | 0 | 9  | 9 | 9 |
| D  | 250 | 0 | 0  | 0 | 0 |

While the invention has been described in detail and with reference to specific embodiments thereof, it will be apparent to one skilled in the art that various changes and modifications can be made therein without departing from the spirit and scope thereof.

What is claimed is:

1. A process for preparing a compound of the formula (VIII-2):

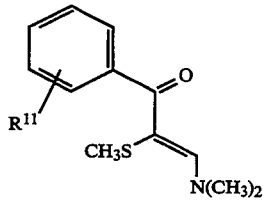

(VIII-2)

wherein $R^{11}$ represents a halo-($C_1$ to $C_6$)-alkoxy group at the ortho or meta position, which comprises reacting a compound of the formula (VIII-3):

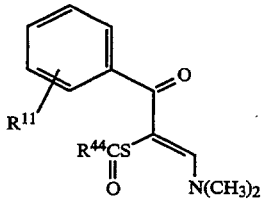

(VIII-3)

wherein $R^{11}$ is as defined above and $R^{44}$ is a ($C_1$ to $C_3$)-alkoxy group, with a compound of the following formula:

CH$_3$I in the presence of a base.

2. A process for preparing a compound of the formula (VIII-3):

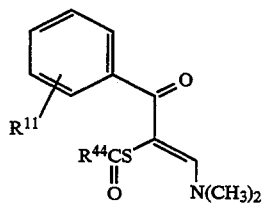

(VIII-3)

wherein $R^{11}$ represents a halo-($C_1$ to $C_6$)-alkoxy group at the ortho or meta position and $R^{44}$ is a ($C_1$ to $C_3$)-alkoxy group, which comprises reacting a compound of the formula (XI):

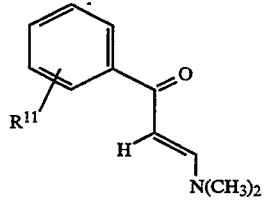

(XI)

wherein $R^{11}$ is as defined above, with a compound of the formula (XII):

(XII)

wherein $R^{44}$ is as defined above and X is a bromine atom or a chlorine atom.

* * * * *